United States Patent
Burdea et al.

(10) Patent No.: US 11,136,234 B2
(45) Date of Patent: Oct. 5, 2021

(54) REHABILITATION SYSTEMS AND METHODS

(71) Applicant: Bright Cloud International Corp., Highland Park, NJ (US)

(72) Inventors: Grigore C. Burdea, Highland Park, NJ (US); Nam Hun Kim, Paramus, NJ (US); Doru Tadeusz Roll, Long Beach, NY (US)

(73) Assignee: Bright Cloud International Corporation, Highland Park, NJ (US)

( * ) Notice: Subject to any disclaimer, the term of this patent is extended or adjusted under 35 U.S.C. 154(b) by 369 days.

(21) Appl. No.: 15/872,964

(22) Filed: Jan. 16, 2018

(65) Prior Publication Data

US 2018/0237284 A1 Aug. 23, 2018

Related U.S. Application Data

(63) Continuation-in-part of application No. 14/575,519, filed on Dec. 18, 2014, now Pat. No. 9,868,012, which is a continuation of application No. 12/192,848, filed on Aug. 5, 2008, now Pat. No. 7,762,434.

(60) Provisional application No. 60/964,861, filed on Aug. 15, 2007.

(51) Int. Cl.
*A61F 5/00* (2006.01)
*B67D 7/02* (2010.01)

(52) U.S. Cl.
CPC .............. *B67D 7/0227* (2013.01); *A61F 5/00* (2013.01); *B67D 7/0238* (2013.01)

(58) Field of Classification Search
CPC ........ B67D 7/0227; B67D 7/0238; A61F 5/00

USPC ......................................................... 434/247
See application file for complete search history.

(56) References Cited

U.S. PATENT DOCUMENTS

| | | |
|---|---|---|
| 4,002,165 A | 1/1977 | Lind |
| 4,337,050 A | 6/1982 | Engalitcheff, Jr. |
| 4,375,674 A | 3/1983 | Thornton |
| 4,471,957 A | 9/1984 | Engalitcheff, Jr. |
| 4,637,789 A | 1/1987 | Netznik |
| 4,773,639 A | 9/1988 | Graves |
| 4,861,051 A | 8/1989 | Napper |
| 4,885,687 A | 12/1989 | Carey |
| 4,976,426 A | 12/1990 | Szabo |
| 5,186,695 A | 2/1993 | Mangseth |
| 5,241,952 A | 9/1993 | Ortiz |

(Continued)

OTHER PUBLICATIONS

Office Action dated Aug. 18, 2011, issued in connection with U.S. Appl. No. 12/192,818 (20 pages).

(Continued)

*Primary Examiner* — Robert P Bullington
(74) *Attorney, Agent, or Firm* — McCarter & English, LLP

(57) ABSTRACT

The present disclosure integrates an actuated tilting rehabilitation table, video tracking of the patient arm and opposite shoulder, a low-friction forearm support with grasping force sensing, remote data transmission and additional weighing means, one or more large displays, a computer and a plurality of simulation exercises, such as video games. The patient can be monitored by a local or remote clinician. The table tilts in order to increase exercise difficulty due to gravity loading on the patient's arm and shoulder. In one embodiment, the actuated tilting table tilts in four degrees of freedom.

14 Claims, 28 Drawing Sheets

(56) References Cited

U.S. PATENT DOCUMENTS

| | | | |
|---|---|---|---|
| 5,265,589 A | 11/1993 | Wang | |
| 5,350,304 A | 9/1994 | Fula | |
| 5,435,728 A | 7/1995 | Fula | |
| 5,466,213 A | 11/1995 | Hogan | |
| 5,518,475 A | 5/1996 | Garland | |
| 5,692,517 A | 12/1997 | Junker | |
| 5,700,201 A | 12/1997 | Bellows | |
| 5,728,030 A | 3/1998 | Hsieh | |
| 5,827,072 A | 10/1998 | Neufer | |
| 5,846,086 A | 12/1998 | Bizzi | |
| 5,871,445 A * | 2/1999 | Bucholz | A61B 5/0064 600/407 |
| 5,913,749 A | 6/1999 | Harmon | |
| 5,954,621 A | 9/1999 | Joutras | |
| 5,976,063 A | 11/1999 | Joutras | |
| 5,980,435 A | 11/1999 | Joutras | |
| 5,986,224 A | 11/1999 | Kent | |
| 6,162,189 A | 12/2000 | Girone | |
| 6,302,037 B1 | 10/2001 | Del Frari | |
| 6,334,778 B1 | 1/2002 | Brown | |
| 6,413,190 B1 | 7/2002 | Wood | |
| 6,416,447 B1 | 7/2002 | Harmon | |
| 6,454,681 B1 | 9/2002 | Brassil et al. | |
| 6,592,315 B2 | 7/2003 | Osborne, Jr. | |
| 6,613,000 B1 | 9/2003 | Reinkensmeyer | |
| 6,682,139 B2 | 1/2004 | Bellows | |
| 6,685,480 B2 | 2/2004 | Nishimoto | |
| 6,749,432 B2 | 6/2004 | French | |
| 6,817,864 B1 | 11/2004 | Martinez | |
| 7,204,814 B2 | 4/2007 | Peles | |
| 7,252,644 B2 | 8/2007 | Dewald | |
| 7,257,237 B1 | 8/2007 | Luck et al. | |
| 7,394,459 B2 | 7/2008 | Bathiche | |
| 7,401,783 B2 | 7/2008 | Pryor | |
| 7,452,336 B2 | 11/2008 | Thompson | |
| 7,476,102 B2 | 1/2009 | Maples | |
| 7,523,984 B2 | 4/2009 | Steininger | |
| 7,525,538 B2 | 4/2009 | Bathiche | |
| 7,648,473 B1 | 1/2010 | Peruvingal | |
| 7,725,175 B2 | 5/2010 | Koeneman | |
| 7,856,264 B2 | 12/2010 | Firlik | |
| 7,880,717 B2 | 2/2011 | Berkley | |
| 7,907,128 B2 | 3/2011 | Bathiche | |
| 8,012,108 B2 | 9/2011 | Bonutti | |
| 9,351,857 B2 | 5/2016 | Carignan | |
| 9,724,598 B2 | 8/2017 | Burdea | |
| 9,868,012 B2 | 1/2018 | Burdea et al. | |
| 10,722,784 B2 | 7/2020 | Burdea et al. | |
| 2001/0034014 A1 | 10/2001 | Nishimoto et al. | |
| 2002/0103429 A1 | 8/2002 | deCharms | |
| 2002/0143277 A1 | 10/2002 | Wood | |
| 2002/0169058 A1 | 11/2002 | Harmon | |
| 2003/0028130 A1 | 2/2003 | Wunderly | |
| 2003/0077556 A1 | 4/2003 | French et al. | |
| 2003/0120183 A1 | 6/2003 | Simmons | |
| 2004/0006287 A1 | 1/2004 | Epley | |
| 2005/0065452 A1 | 3/2005 | Thompson | |
| 2005/0091749 A1 | 5/2005 | Humbles | |
| 2005/0113652 A1 | 5/2005 | Stark et al. | |
| 2005/0167907 A1 | 8/2005 | Curkendall | |
| 2005/0181347 A1 | 8/2005 | Barnes | |
| 2005/0187071 A1 | 8/2005 | Yamashita | |
| 2005/0216243 A1 | 9/2005 | Graham et al. | |
| 2005/0283053 A1 | 12/2005 | deCharms | |
| 2006/0001296 A1 | 1/2006 | Riach | |
| 2006/0003877 A1 | 1/2006 | Harmon | |
| 2006/0079817 A1 | 4/2006 | Dewald et al. | |
| 2006/0161218 A1 | 7/2006 | Danilov | |
| 2006/0195018 A1 | 8/2006 | Guillen | |
| 2006/0241718 A1 | 10/2006 | Tyler | |
| 2006/0293617 A1 | 12/2006 | Einav | |
| 2007/0003915 A1 | 1/2007 | Templeman | |
| 2007/0043308 A1 | 2/2007 | Lee | |
| 2007/0060445 A1 | 3/2007 | Reinkensmeyer | |
| 2007/0060849 A1 | 3/2007 | Bluman | |
| 2007/0066918 A1 | 3/2007 | Dewald | |
| 2007/0087901 A1 | 4/2007 | Brassil et al. | |
| 2007/0100214 A1 | 5/2007 | Steinert | |
| 2007/0136093 A1 | 6/2007 | Rankin et al. | |
| 2007/0191141 A1 | 8/2007 | Weber | |
| 2007/0250119 A1 | 10/2007 | Tyler | |
| 2007/0254787 A1 | 11/2007 | Matsubara | |
| 2007/0282228 A1 | 12/2007 | Einav | |
| 2008/0004550 A1 | 1/2008 | Einav | |
| 2008/0009771 A1 | 1/2008 | Perry | |
| 2008/0009772 A1 | 1/2008 | Tyler | |
| 2008/0036737 A1 | 2/2008 | Hernandez-Rebollar | |
| 2008/0061949 A1 | 3/2008 | Ferguson et al. | |
| 2008/0132383 A1 | 6/2008 | Einav | |
| 2008/0139975 A1 | 6/2008 | Einav | |
| 2008/0242521 A1 | 10/2008 | Einav | |
| 2008/0281633 A1 | 11/2008 | Burdea | |
| 2008/0319349 A1 | 12/2008 | Zilberman | |
| 2009/0023122 A1 | 1/2009 | Lieberman | |
| 2009/0062698 A1 | 3/2009 | Einav | |
| 2009/0091229 A1 | 4/2009 | Karl | |
| 2009/0131225 A1 * | 5/2009 | Burdea | A63B 21/06 482/5 |
| 2009/0227888 A1 | 9/2009 | Salmi | |
| 2009/0233769 A1 | 9/2009 | Pryor | |
| 2009/0305207 A1 | 12/2009 | Ueshima | |
| 2010/0016766 A1 | 1/2010 | Zhang | |
| 2010/0068686 A1 | 3/2010 | Ueshima | |
| 2010/0125033 A1 | 5/2010 | Harmon | |
| 2010/0179453 A1 | 7/2010 | Schweighofer | |
| 2010/0182220 A1 | 7/2010 | Bathiche | |
| 2010/0204616 A1 | 8/2010 | Shears | |
| 2010/0234182 A1 | 9/2010 | Hoffman | |
| 2010/0271315 A1 | 10/2010 | Bathiche | |
| 2011/0112441 A1 | 5/2011 | Burdea | |
| 2011/0167563 A1 | 7/2011 | Humbles | |
| 2011/0319166 A1 | 12/2011 | Bathiche | |
| 2012/0108909 A1 | 5/2012 | Slobounov et al. | |
| 2012/0157263 A1 | 6/2012 | Sivak et al. | |
| 2013/0061395 A1 | 3/2013 | Karl | |
| 2013/0109549 A1 | 5/2013 | Harmon | |
| 2015/0099614 A1 | 4/2015 | Tekulve | |
| 2015/0105222 A1 | 4/2015 | Burdea et al. | |
| 2016/0038075 A1 | 2/2016 | Burdea et al. | |
| 2016/0144229 A1 | 5/2016 | Aluru | |
| 2016/0166451 A1 | 6/2016 | Tekulve | |
| 2018/0214761 A1 | 8/2018 | Olds et al. | |
| 2018/0228407 A1 | 8/2018 | Olds et al. | |

OTHER PUBLICATIONS

Office Action dated Apr. 11, 2012, issued in connection with U.S. Appl. No. 12/192,818 (14 pages).

Office Action dated Jun. 18, 2014, issued in connection with U.S. Appl. No. 12/192,818 (19 pages).

Office Action dated Jul. 29, 2016, issued in connection with U.S. Appl. No. 14/575,519 (22 pages).

Office Action dated Feb. 9, 2017, issued in connection with U.S. Appl. No. 14/575,519 (16 pages).

Applicant-Initiated Interview Summary dated Jul. 7, 2017, issued in connection with U.S. Appl. No. 14/575,519 (3 pages).

Notice of Allowance dated Sep. 11, 2017, issued in connection with U.S. Appl. No. 14/575,519 (9 pages).

Ausenda, CD., et al., "Transfer of Motor Skill Learning from the Healthy Hand to the Paretic Hand in Stroke Patients: A Randomized Controlled Trial," Eur. J. Rehabil Med., 2011; vol. 47(3), pp. 417-425.

Brooks, CA., et al., "Traumatic Brain Injury: Designing and Implementing a Population-Based Follow-Up System," Arch Phys Med. Rehabil. 1997; vol. 78(8), pp. 26-30.

Burdea et al., The Rutgers Arm II Rehabilitation System, Jul. 23, 2008.

Burdea, GC., et al., "The Rutgers Arm II Rehabilitation System—A Feasibility Study," IEEE Trans Neural Sys Rehab Eng., vol. 18(5), pp. 505-514.

Burdea, GC., "Virtual Rehabilitation-Benefits and Challenges," Methods Inf Med. 2003; vol. 42(5), pp. 519-523.

(56) References Cited

OTHER PUBLICATIONS

Burke, J.W., et al., "Optimising Engagement for Stroke Rehabilitation Using Serious Games," Vis. Comput, 2009, pp. 1085-1099.
Cameirao MS, et al., "The Rehabilitation Gaming System: A Review,". Stud Health Technol Inform. 2009; vol. 145, pp. 65-83. PubMed PMID: 19592787.
Cameirao, et al., "Neurorehabilitation Using the Virtual Reality Based Rehabilitation Gaming System: Methodology, Design, Psychometrics, Usability and Validation" 2010 (14 pages).
Cauraugh, JH., et al., "Bilateral Movement Training and Stroke Motor Recovery Progress: A Structured Review and Meta-Analysis," Hum. Mov. Sci., 2010; vol. 29(5), pp. 853-870.
Chen et al., Aid Training System for Upper Extremity Rehabilitation, 2001 Proceedings of the 23rd Annual EMBS International Conference, Oct. 25-28, 2001.
CNet Leap Motion Controller Review: Virtual Reality for Your Hands, Jul. 22, 2013 http://www.cnet.com/products/leap-motion-controller/ (9 pages).
Colombo G, et al., "Novel tilt table with integrated robotic stepping mechanism: Design principles and clinical application", Proceedings of the 2005 IEEE, 9th International Conference on Rehabilitation Robotics, 2005, pp. 227-230.
Colombo R, et al., "Upper limb rehabilitation and evaluation of stroke patients using robot-aided techniques", Proceedings of the 2005 IEEE, 9th Internaitonal Conference on Rehabilitation Robotics, 2005, pp. 515-518.
Dewald et al., Upper-Limb Discoordination in Hemiparetic Stroke: Implications for Neurorehabilitation, Top Stroke Rehabil, 2001; vol. 8(1), pp. 1-12.
Duncan, PW., et al., "Reliability of the Fugl-Meyer Assessment of Sensorimotor Recovery Following Cerebrovascular Accident," Phys Ther., 1983; vol. 63(10), pp. 1606-1610.
House, G et al. "A feasibility study to determine the benefits of upper extremity virtual rehabilitation therapy for coping with chronic pain post-cancer surgery " The British Journal of Pain, Nov. 2016, vol. 10(4), pp. 186-197.
House, G et al. "Integrative rehabilitation of stroke survivors in skilled nursing facilities: the design and evaluation of the BrightArm Duo." Disability and Rehabilitation-Assistive Technology. Nov. 2016. vol. 11(8), pp. 683-694.
House, G. et al. "Integrative Virtual Reality Therapy Produces Lasting Benefits for a Young Woman Suffering from Chronic Pain and Depression Post Cancer Surgery: A Case Study." 11th Int Conference on Disability and Virtual Reality Technology, Sep. 2016. (9 pages).
Kim S.H., et al., "An intelligent tilt table for paralytic patients", Biomed 06, IFMBE Proceedings, 2007, vol. 15, pp. 615-617.
Kuttuva M, et al., "The Rutgers Arm: An upper-extremity rehabilitation system in virtual reality", Fourth Int. Workshop on Virtual Rehabilitation, 2005, pp. 1-8.
Lin, KC., et al., "The Effects of Bilateral Arm Training on Motor Control and Functional Performance in Chronic Stroke: A Randomized Controlled Study," Neurorehabil Neural Repair, 2010; vol. 24(1), pp. 42-51.
Liu, Huajun, et al. "Realtime human motion control with a small number of inertial sensors." Symposium on Interactive 3D Graphics and Games. ACM, 2011 (8 pages).
Loureiro et al., Robot Aided Therapy: Challenges Ahead for Upper Limb Stroke Rehabilitation, Proc. 5th Intl. Conf. Disability, Virtual Reality & Assoc. Tech., Oxford, UK, 2004.
Optale, G., et al., "Controlling Memory Impairment in Elderly Adults Using Virtual Reality Memory Training: A Randomized Controlled Pilot Study," Neurorehabil Neural Repair, 2010; vol. 24(4), pp. 348-357.
Rabadi, MH, et al., "Intensive Nutritional Supplements Can Improve Outcomes in Stroke Rehabilitation," Neurology, 2008, pp. 1856-1861.
Roger, VL., et al., "Executive Summary: Heart Disease and Stroke Statistics—2012 Update: A Report from the American Heart Association," Circulation, 2012; vol. 125(1), pp. 188-197.
Sixense Entertainment, Razer Hydra Master Guide, 2011, pp. 1-11.
Wang, M., et al., "Neuronal Basis of Age-Related Working Memory Decline," Nature, 2011; vol. 476(7359), pp. 210-213.
Wu, CY. et al., "Randomized Trial of Distributed Constraint-Induced Therapy Versus Bilateral Arm Training for the Rehabilitation of Upper-Limb Motor Control and Function After Stroke," Neurorehabil Neural Repair, 2011, vol. 25(2), pp. 130-139.

* cited by examiner

REHABILITATION SYSTEMS AND METHODS

CROSS-REFERENCE TO RELATED APPLICATIONS

The present application is a continuation-in-part of U.S. patent application Ser. No. 14/575,519, filed Dec. 18, 2014, now U.S. Pat. No. 9,868,012 which is a continuation of U.S. patent application Ser. No. 12/192,818, filed Aug. 15, 2008, both of which claim the benefit of and priority to U.S. Provisional Patent Application No. 60/964,861, filed Aug. 15, 2007, all of which are hereby incorporated by reference in their entirety.

GOVERNMENT LICENSE RIGHTS

This invention was made with government support under grant 2R44AG044639-04 awarded by The National Institutes of Health. The United States government has certain rights in the invention.

BACKGROUND

Field

The present disclosure is a device, system and method of providing rehabilitation to several types of patients in a rehabilitation hospital or outpatient clinic. The approach integrates an actuated tilting and lifting low-friction rehabilitation table, video or infrared tracking of the patient's arm, or arms, and opposite shoulder, one or two low-friction forearm support(s) with grasping force sensing and finger extension sensing, remote data transmission and additional weighting means, one or more large displays, a computer, a control box, and a plurality of video games.

Related Art

A training system for arm rehabilitation is described in Yu-Luen Chen et al., "Aid Training System for Upper Extremity Rehabilitation," 2001 Proceedings of the EMBS International Conference, Istanbul, Turkey. Patients exercise on a special table that incorporates reed relays and a hand support ("arm skate") with small underside wheels. The movement of the arm in the arm skate on the supporting table is detected by the interaction of the magnet incorporated in the arm skate with the relays integrated in the table. A computer presents a variety of patterns on its monitor, which the patient needs to replicate to improve arm coordination, with performance data stored by the computer in a clinical database. The table is horizontal, not tilted, and does not use virtual reality simulations.

Another training system that uses a forearm support on a table for rehabilitation purposes is described by some of the inventors of the present specification in Kutuva et al., "The Rutgers Arm: An Upper-Extremity Rehabilitation System in Virtual Reality," Proceedings of the Fourth International Workshop on Virtual Rehabilitation (IWVR '05), pp. 94-103, Catalina Island, Calif., September 2005. The table has a low-friction surface and a forearm support has a low-friction underside (made of TEFLON® studs). The tracking of the forearm movement is done by a magnetic tracker (Fastrack, Polhemus Inc.), with a sensor mounted on the forearm support, and an emitter mounted on the table away from the patient. Patients exercise sitting at the table and looking at a computer monitor, while playing a plurality of virtual reality games. The games are designed to improve motor coordination, as well as dynamic arm response. The table does not tilt.

Several tilting tables exist commercially and are used in rehabilitation. They are meant for people who have low blood pressure and who get dizzy when they stand up. Tilting tables are also used for the rehabilitation of patients who have to lie down for a long period of time. The person lies face up on a padded table with a footboard and is held in place with a safety belt. The table is tilted so that the angle is very slowly increased until the person is nearly upright. By slowly increasing the angle, the patient's blood vessels regain the ability to constrict.

A study describes development of a sensorized tilt table which measures and displays the knee bent angle and pressure for each foot during exercise in real time, as described in Kimet et al. "An Intelligent Tilt Table for Paralytic Patients," $3^{rd}$ Kuala Lumpur International Conference on Biomedical Engineering, Kuala Lumpur, Malaysia, 2006. It is expected that the patient's exercising effect can increase by monitoring these two values during exercise. Tilt tables are known for providing tilting manually or using an electrical motor, such as in a Rehab Electric Tilt Table manufactured by Cardon Rehab.

An automated stepping training developed with the tilting table is described in Colombo et al. "Novel Stepping Mechanism: Design Principles and Clinical Application," Rehabilitation Robotics, ICORR 2005. Unlike the previous tilting tables it exercises the feet in stepping. No virtual reality simulation is incorporated and tilting is done manually, rather than determined by a simulation.

All of the above tilting-table based systems are for rehabilitation of the legs. The tilting tables described above do not incorporate virtual reality simulations and do not store/upload clinical data automatically. They have a single degree of freedom (the tilting angle).

Some of the inventors have used the BrightArm Duo tilting and lifting rehabilitation table for rehabilitation of chronic stroke survivors who are long term nursing home residents. House G, G. Burdea, K. Polistico, D. Roll, J. Kim, F. Damiani M D, S. Keeler, J. Hundal, S. Pollack. Integrative rehabilitation of stroke survivors in Skilled Nursing Facilities: the design and evaluation of the BrightArm Duo. *Disability and Rehabilitation-Assistive Technology*. November 2016. 11 (8):683-94. Patients exercise both arms supported by forearm supports while playing adaptable games. The system is designed to train both arms and mind. Two overhead cameras are used to track the forearms of the patients and are located on an overhead beam that maintains camera orientation versus the table surface regardless of tilt. Arm reach and grasp strength are measured at the start of session so as to adapt games to dissimilar arm capabilities. A similar setting was used for patients with chronic upper body pain, which affects the motor function, strength and range of the arms. House G, G Burdea, N Grampurohit, K Polistico, D Roll, F Damiani, J Hundal, D Demesmin. Integrative Virtual Reality Therapy Produces Lasting Benefits for a Young Woman Suffering from Chronic Pain and Depression Post Cancer Surgery: A Case Study. 11*th Int Conference on Disability and Virtual Reality Technology*, September 2016, Los Angeles. Since chronic pain is also associated with depression, study results have shown a reduction of depression severity in a group of 6 breast cancer survivors after 8 weeks of therapy on the BrightArm Duo. House G, Burdea G, N Grampurohit, K Polistico, D Roll, F Damiani, J Hundal, D Demesmin. A feasibility study to determine the benefits of upper extremity virtual rehabilitation therapy for coping with chronic pain post-cancer surgery. *The British Journal of Pain*, November 2016, 10(4): 186-197. doi 10.1177/2049463716664370.

Systems for rehabilitating the arms are known, and are based on force feedback joysticks (such as those manufactured by Logitech or Microsoft), or various types of planar or 3D robots. Examples of planar robots are the MIT Manus or those described in Colombo et al., "Upper Limb Rehabilitation and Evaluation of Stroke Patients Using Robot-Aided Techniques", Rehabilitation Robotics, 515-518 (2005). Other examples of 3D robots are the Reo robot manufactured by Motorika, N.J., or the Haptic Master manufactured by FCS, Holland.

Other upper limb rehabilitation systems have been described. U.S. Pat. No. 7,204,814 describes an orthotic system that performs predefined or user-controlled limb movements, collects data regarding the limb movement, performs data analysis and displays the data results, modifies operational parameters based on the data to optimize the rehabilitative process performed by the system. A force sensor data, torque data and angular velocity data can be collected using an external actuating device.

U.S. Patent Application Publication No. 2007/0060445 describes a method and apparatus for upper limb rehabilitation training of coordinated arm/forearm, forearm/forearm, and grasping movements comprising a non-robotic, passive support, an arm/forearm sensor, gripping device and sensor. A computer processes measurements of movements to control a graphical representation of the arm/forearm and grasping movements in interaction with a virtual environment.

It is desirable to provide a device, system and method for rehabilitation of one or both upper limbs in which an activated low-friction tilting and lifting table provides a plurality of degrees of freedom and grasping force and finger extension sensing are integrated into a video tracking system.

SUMMARY

The present disclosure integrates an actuated tilting and lifting rehabilitation table, video tracking of one or both of the patient arm(s) and shoulder, low-friction forearm supports with grasping force and finger extension sensing, remote data transmission and additional weighing means, one or more large displays, a computer, a control box, and a plurality of simulation exercises, such as therapeutic video games. The patient can be monitored by a local or remote clinician. Online storage of data obtained by the rehabilitation tilting table can be provided. Automated session report can be generated. Additionally, the table surface can be constructed as a graphics display making a separate display unnecessary.

In one embodiment, a patient's arm rests on a forearm support that has infrared LEDs. The patient wears similar LEDs on the opposite shoulder, and an infrared video camera is used to track the patient's arm movement on the table. The table tilts in order to increase exercise difficulty due to gravity loading on the patient's arm. In one embodiment, the present the invention includes an actuated tilting table which tilts in four degrees of freedom. A large display, facing the patient presents a sequence of rehabilitation games with which the patient interacts by moving the arm resting on the low-friction support, on the table surface.

In another embodiment the patient sits in a wheel chair, while resting both arms which are tracked by infrared trackers, such as those available commercially. The shape of the table surface is such as to accommodate the trunk of the patient seated at the table. The underside of the table has a safety mechanism to detect a proximity of the knees and legs of a patient. The table actuators are elevated from the table frame, so as to allow a patient to stretch his or her legs in front of the wheelchair.

BRIEF DESCRIPTION OF THE DRAWINGS

The foregoing features of the present disclosure will be apparent from the following Detailed Description of the Invention, taken in connection with the accompanying drawings, in which.

DETAILED DESCRIPTION

Figure 1:
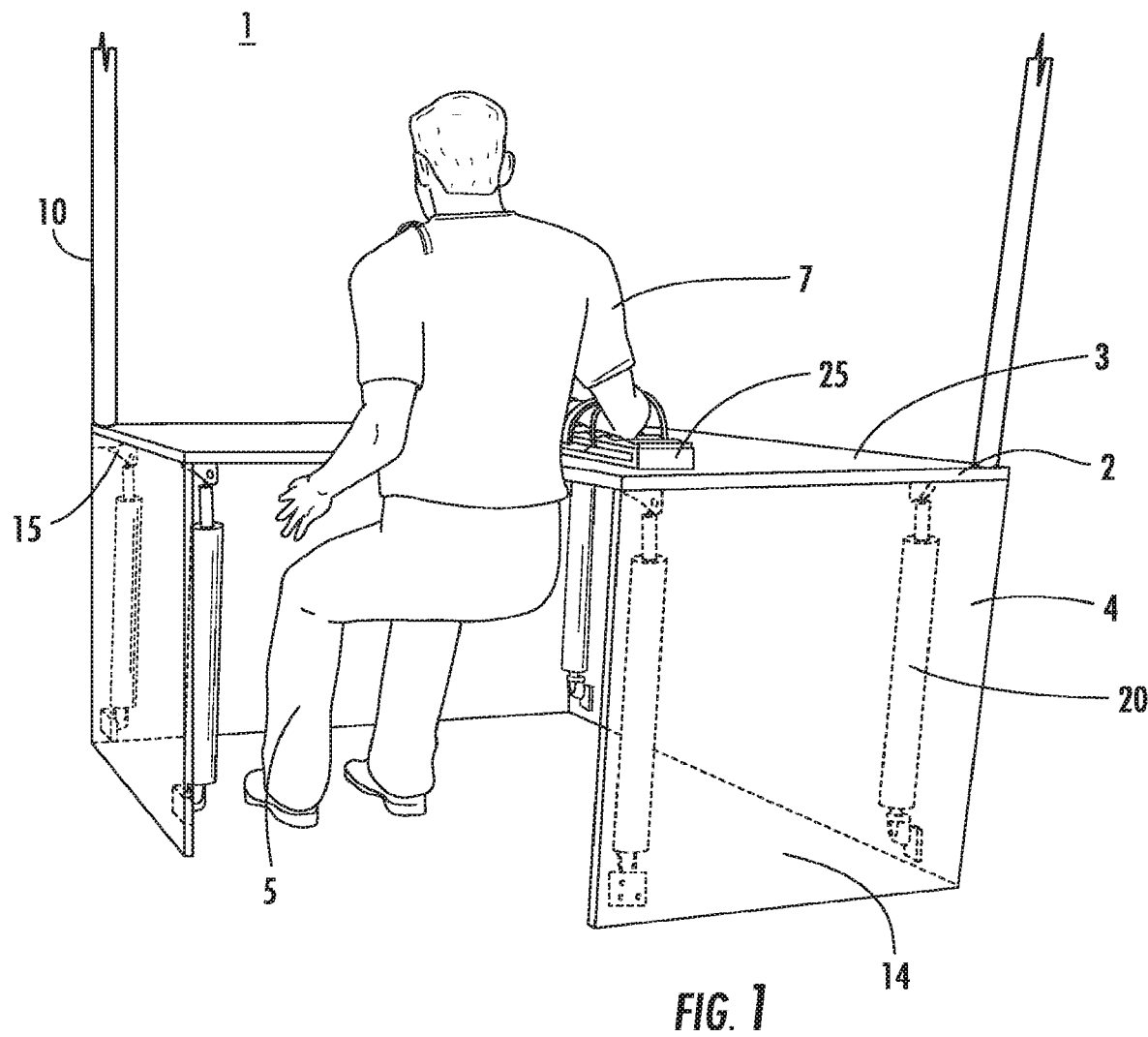
FIG. 1 is a schematic diagram of a tilting rehabilitation table system being used by a patient.

Reference will now be made in greater detail to a preferred embodiment of the invention, an example of which is illustrated in the accompanying drawings. Whenever possible, the same reference numerals will be used throughout the drawings and the description to refer to the same or like parts.

Figure 2:
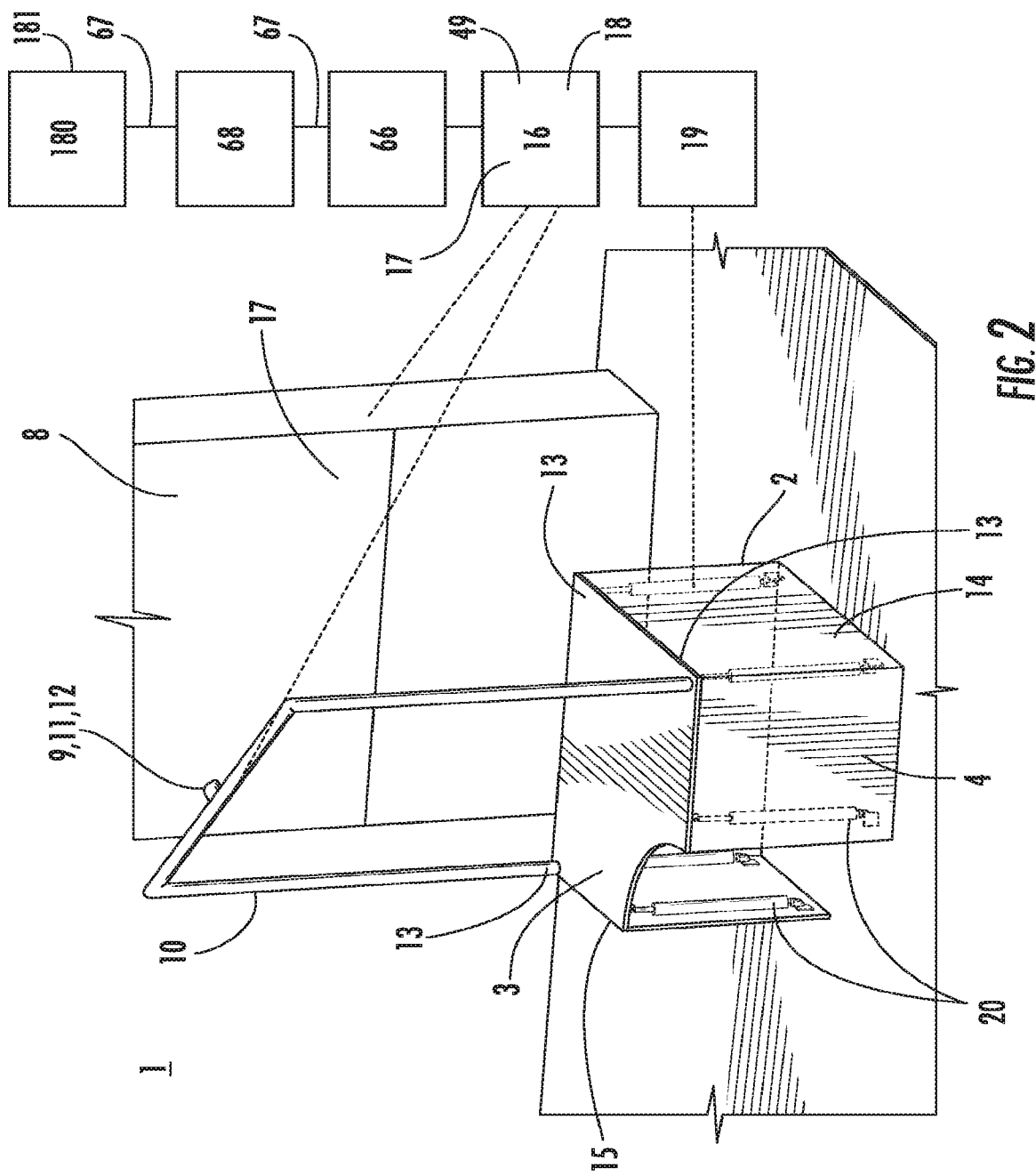
FIG. 2 is a schematic diagram of the tilting rehabilitation table system.

FIGS. 1 and 2 illustrate tilting rehabilitation table system 1. Tilting rehabilitation table system 1 incorporates tilting table 2 which has top surface 3 and underside surface 4. Top surface 3 can be a U-shaped, symmetrical, low-friction surface. Underside surface 4 can have a U-shape. For example, low top surface 3 can be made of carbon fiber, or other durable and light material, covered by a low-friction coating. Suitable low-friction coatings include TEFLON® sheets. Underside walls 14 extend upwardly from underside surface 4.

Patient 5 sits in chair 6 and rests arm 7 to be rehabilitated in low-friction forearm support 25. Patient 5 exercises while watching display 8 placed at the opposite side of tilting table 2. Preferably, display 8 is a large display having dimensions of at least about 9 ft by 6 ft. Video camera 9 is attached to vertical support 10. Vertical support 10 can be U-shaped and rigid. Vertical support 10 extends from and is attached to top surface 3. This arrangement allows video camera 9 to view tilting table 2 and patient 5 simultaneously. Video camera 9 can be a conventional digital camera. Infrared filter 11 can be attached to lens 12 of video camera 9. LEDs 13 are mounted at the corners of top surface 3 and can be wired to direct current source (not shown). For example, three LEDs can be used for providing calibration of video camera 9. Vertical support 10 is mounted to top surface 3 such that it keeps the same relative orientation regardless of tilt angle 15 of top surface 3, thereby making re-calibration of video camera 9 unnecessary once tilt angle 15 changes during a rehabilitation session.

Computer 16 renders exercise simulation 17 and displays them on display 8. For example, exercise simulation 17 can be an animated or virtual reality sequence. Computer 16 is preferably a multi-core PC workstation. Computer 16 also receives input from video camera 9. Computer 16 runs tracking software 18 and communicates with controller 19. Controller 19 activates actuators 20 to provide tilt of top surface 3. Computer 16 is connected to Internet 66 and transparently uploads clinical data 67 to remote clinical database server 68. Remote computer 181 connected to clinical database server 68 over Internet 66 is used to execute remote graphing software 180.

Figure 3:
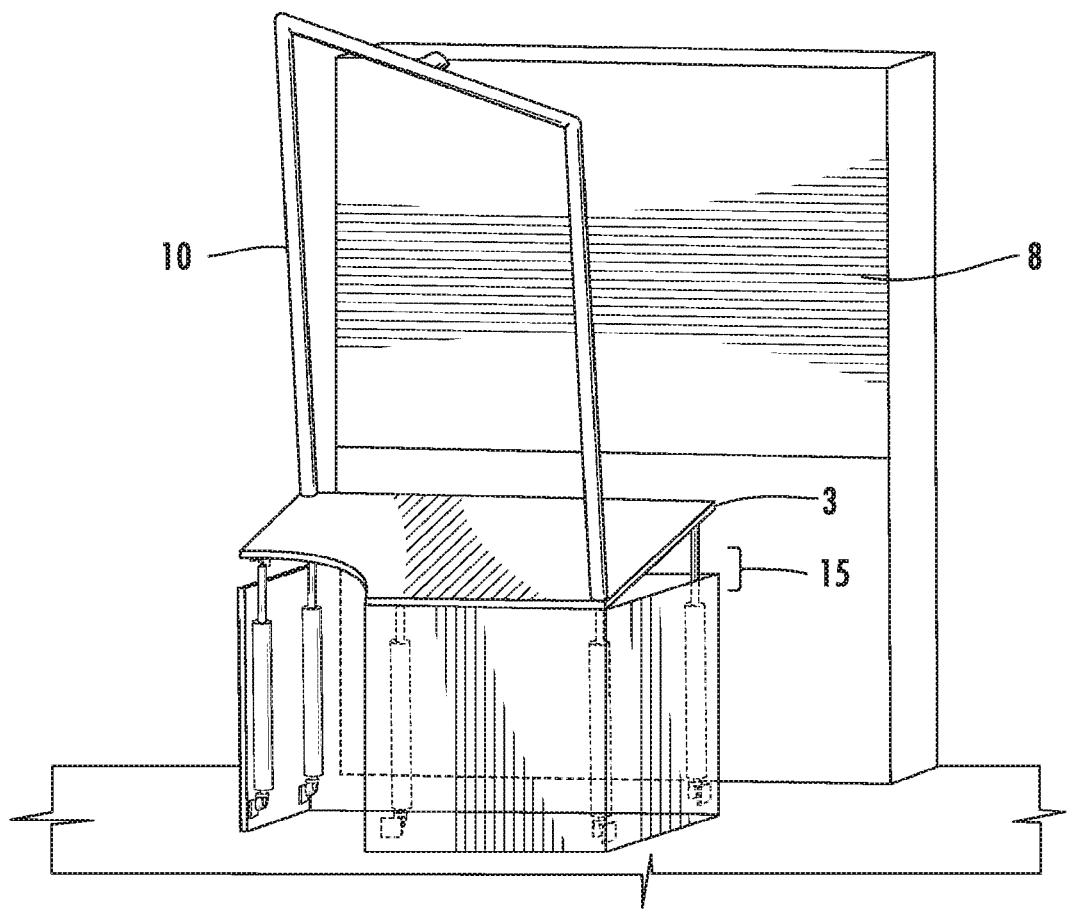
FIG. 3 is a schematic diagram in which a top surface of the tilting table is provided at an increased angle from the patient.

FIG. 3 shows the orientation of top surface 3 and camera support 10 when tilt angle 15 is increased to move the angle away from patient 5. Increased tilt angle 15 makes in/out movements of arm 7 more difficult.

Figure 4:
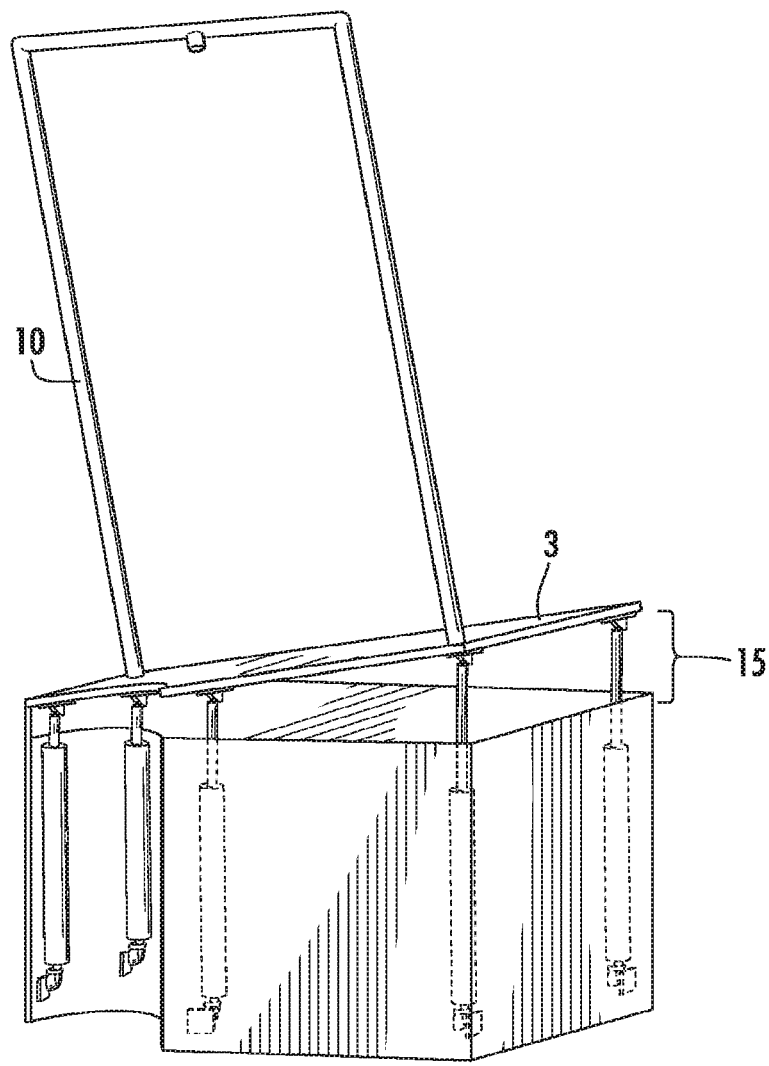
FIG. 4 is a schematic diagram in which the top surface of the tilting table is provided at an increased right angle from the patient.

FIG. 4 shows a different tilt of top surface 3, in which tilt angle 15 is to the right of patient 5. This tilt angle makes arm movements from left-to-right more difficult than those when top surface 3 is horizontal. Other tilt angles 15 can be used when the left side of top surface 3 is tilted up or when the side closer to patient 5 is tilted up. These make more difficult corresponding arm 7 movements, such as right-left or out-in, respectively. In one embodiment, top surface 3 can be tilted in four degrees of freedom.

Figure 5:
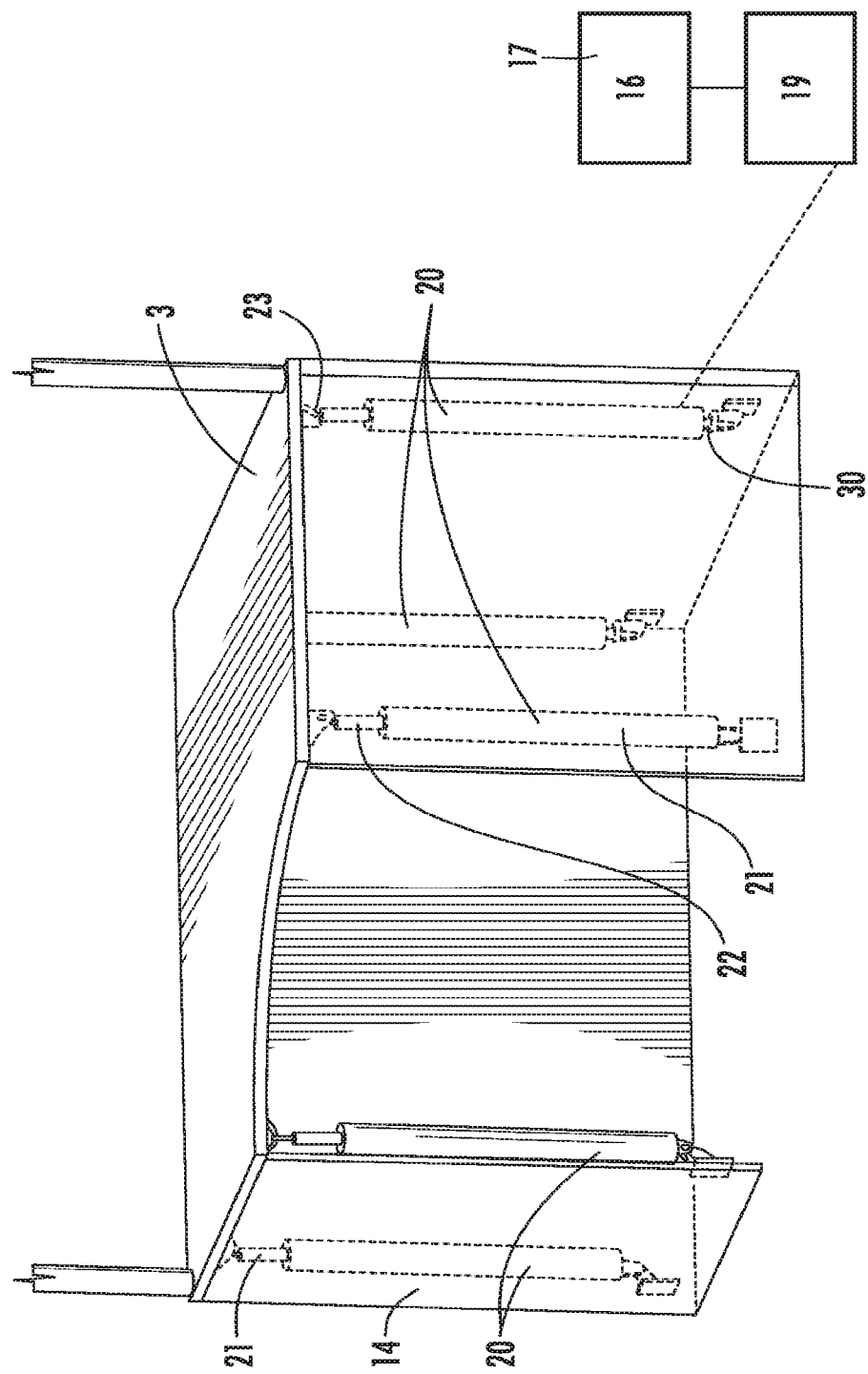
FIG. 5 is a schematic diagram of actuators of the tilting rehabilitation table system used with the tilting table.

Tilt angle 15 is produced by two or more actuators 20 placed under top surface 3, as shown in FIG. 5. Actuators 20 are preferably linear electrical actuators. Actuators 20 are positioned under top surface 3. Each actuator 20 includes base 21 and translating shaft 22. Translating shaft 22 is connected to top surface 3 by top joint assembly 23. Base 21 is connected to underside walls 14 with bottom joint assembly 30. Actuators 20 are controlled by controller 19. Controller 19 can be a multi-channel micro-controller such as those which are available commercially. Controller 19 in turn receives commands from computer 16 running exercise simulation 17. In one embodiment, five actuators 20 can be used and the amount of translation of actuator shaft 22 provides tilt angle 15 which can be varied from about 0 degrees (horizontal) to about 30 degrees. The more top surface 3 is tilted, the larger the effect gravity has due to the weight of arm 7 of patient 5 and of forearm support 25 and the harder exercise simulation 17 is to perform.

Figure 6:
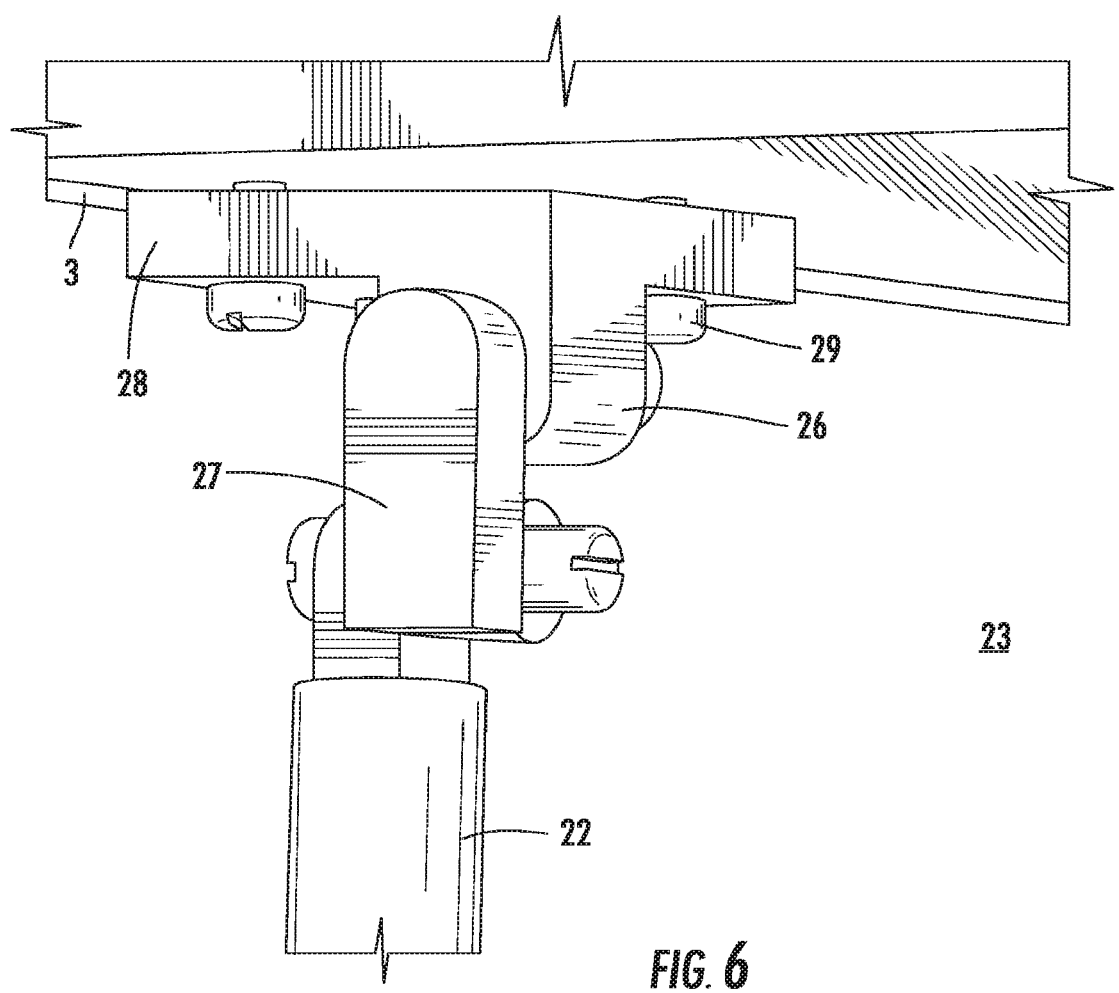
FIG. 6 is a detailed view of a top joint assembly connecting an actuator shaft to the top surface of the tilting table.

FIG. 6 shows a detailed view of top joint assembly 23 which connects actuator shaft 22 to the underside of top surface 3. Top joint assembly 23 has horizontal rotating joint 26 and vertical rotating joint 27 which together produce two degrees of freedom for top joint assembly 23. The axis of rotation of horizontal rotating joint 26 is perpendicular to the axis of rotation of vertical rotating joint 27. Horizontal rotating joint 26 is attached to the underside of top surface 3 using plate 28 and bolts 29.

Figure 7:
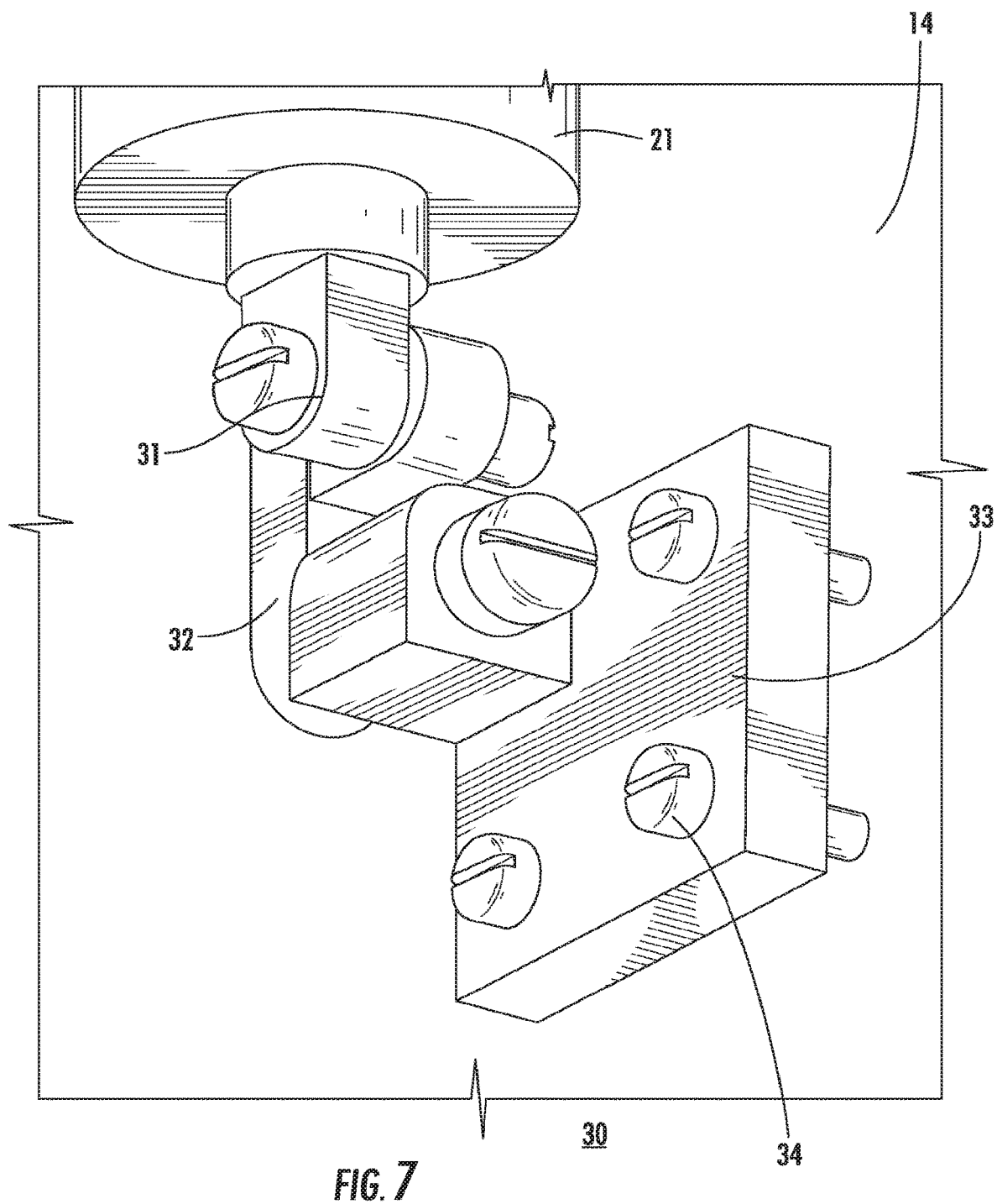
FIG. 7 is a detailed view of a bottom joint assembly connecting an actuator shaft to the bottom surface of the tilting table.

FIG. 7 shows a detailed view of bottom joint assembly 30, which connects base 21 to the inner side of underside walls 14. Bottom joint assembly 30 has horizontal rotating joint 31 and vertical rotating joint 32 which together produce two degrees of freedom for bottom joint assembly 30. The axis of rotation of horizontal rotating joint 31 is perpendicular to the axis of rotation of vertical rotating joint 32. Vertical rotating joint 32 is attached to the inner side of underside walls 14 through plate 33 and bolts 34.

Figure 8:
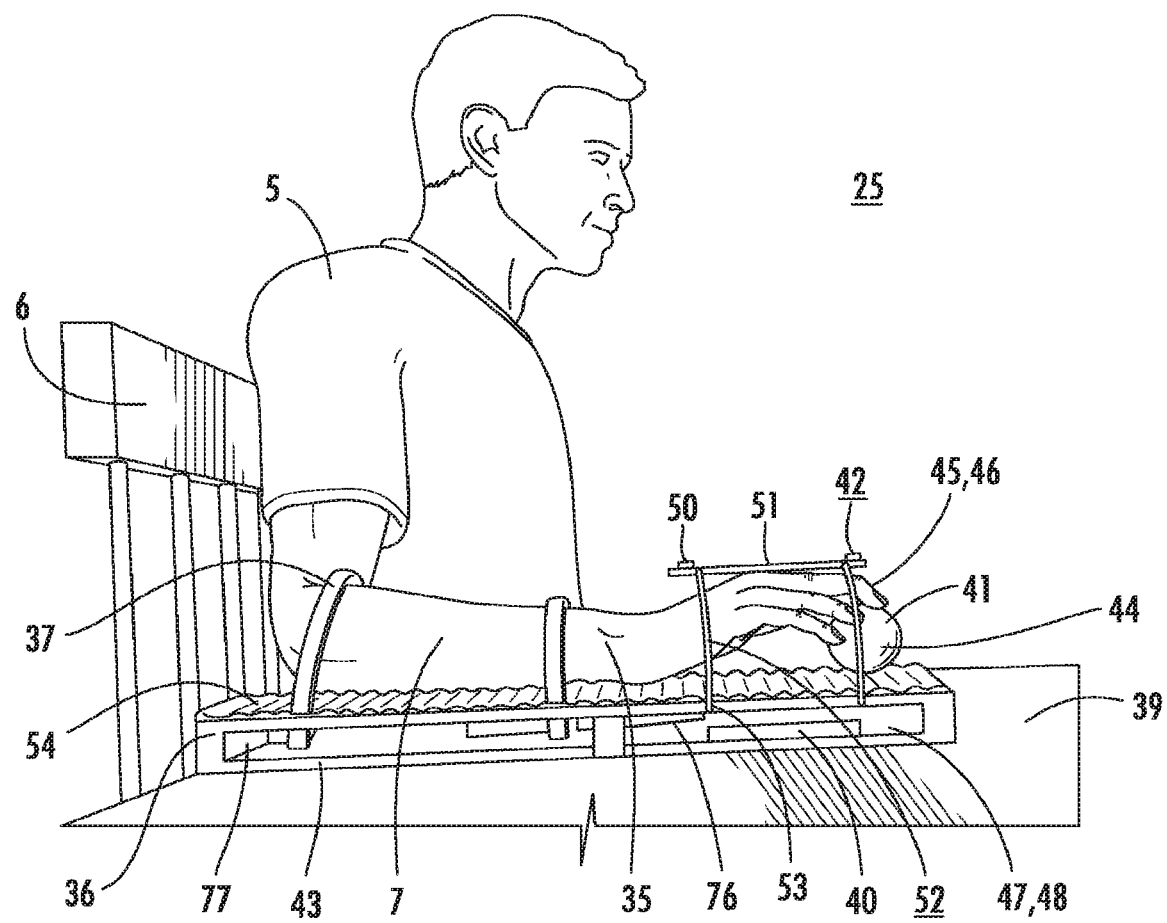
FIG. 8 is a side elevation view of patient wearing the forearm support assembly used in the tilting rehabilitation table system.

A side view of the patient 5 sitting in chair 6 and using of forearm support assembly 25 used by patient 5 is shown in FIG. 8. Forearm 7 and wrist 35 of patient 5 are secured to forearm support base 36 using a plurality of straps 37. For example, straps 37 can be formed of a hook and loop material of VELCRO®. Forearm support base 36 can be made of a lightweight material such as plastic, and is hollow. Pressure sensor 41 measures the air pressure inside hollow compliant element 44. A suitable hollow compliant element 44 can be a rubber ball. Grasping forces 45 exercised by fingers 46 of patient 5 are measured. Video camera 9 shown in FIG. 1 views LED assembly 42 which is formed of two infrared LEDs 50 mounted on plastic support 51 for providing data on arm movements and rotation. LED assembly 42 in turn is mounted on movable assembly 52. Movable assembly 52 rotates on hinges 53 attached to forearm support base 36. Movable assembly 52 rotates open to allow forearm 7 to be placed on forearm support top surface 54. Forearm support top surface 54 is preferably made of a compliant material (such as plastic foam), for increased comfort. Forearm support base 36 has chambers 39, 76 and 77. Chamber 39 can be used to incorporate electronics assembly 40 to which is connected pressure sensor 41. Output of pressure sensor 41 is processed by electronics assembly 40. Electronics assembly 40 includes an analog-to-digital converter 47 and wireless transmitter 48. Transmitter 48 can be a conventional wireless Bluetooth® type transmitter. Transmitter 48 communicates with receiver 49 incorporated in computer 16, as shown in FIG. 2. Computer 16 can change exercise simulation 17 according to grasping forces 45 of patient 5. Computer 16 can also change exercise simulation 17 based on forearm 7 position/orientation given by video camera 9. For example, exercise simulation 17 can be rehabilitation games. LED assembly 42 and electronics assembly 40 are connected to battery 43 in chamber 77. Chamber 76 of base 36 can be used to allow the addition of modular weights 56. The addition of modular weights 56 to forearm support base 36 allows an increased difficulty of exercise simulation 17. The difficulty of performing exercise simulation 17 is increased with the increase in modular weights 56, with the increase in tilting angle 15, and with the number and level of exercise simulation 17.

Figure 9:
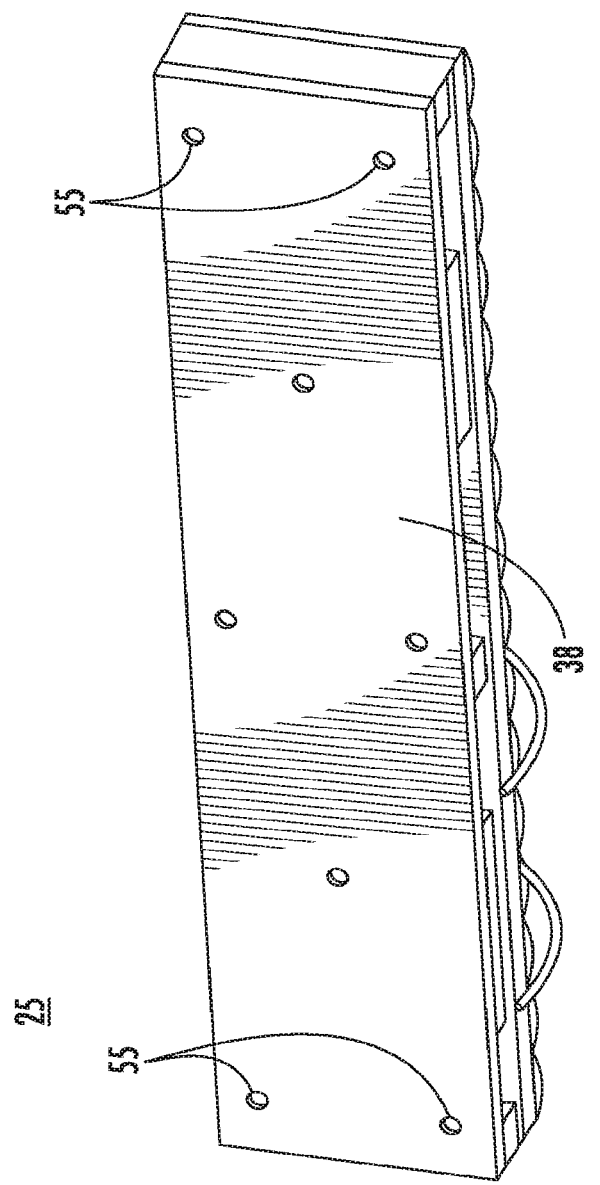
FIG. 9 is a schematic diagram of an underside of a forearm support assembly of the tilting rehabilitation table.

FIG. 9 is a view of the underside of the forearm support assembly 25. Underside surface 38 of forearm support 25 has a plurality of low friction studs 55. Low friction studs 55 are preferably made of TEFLON®.

Figure 10:
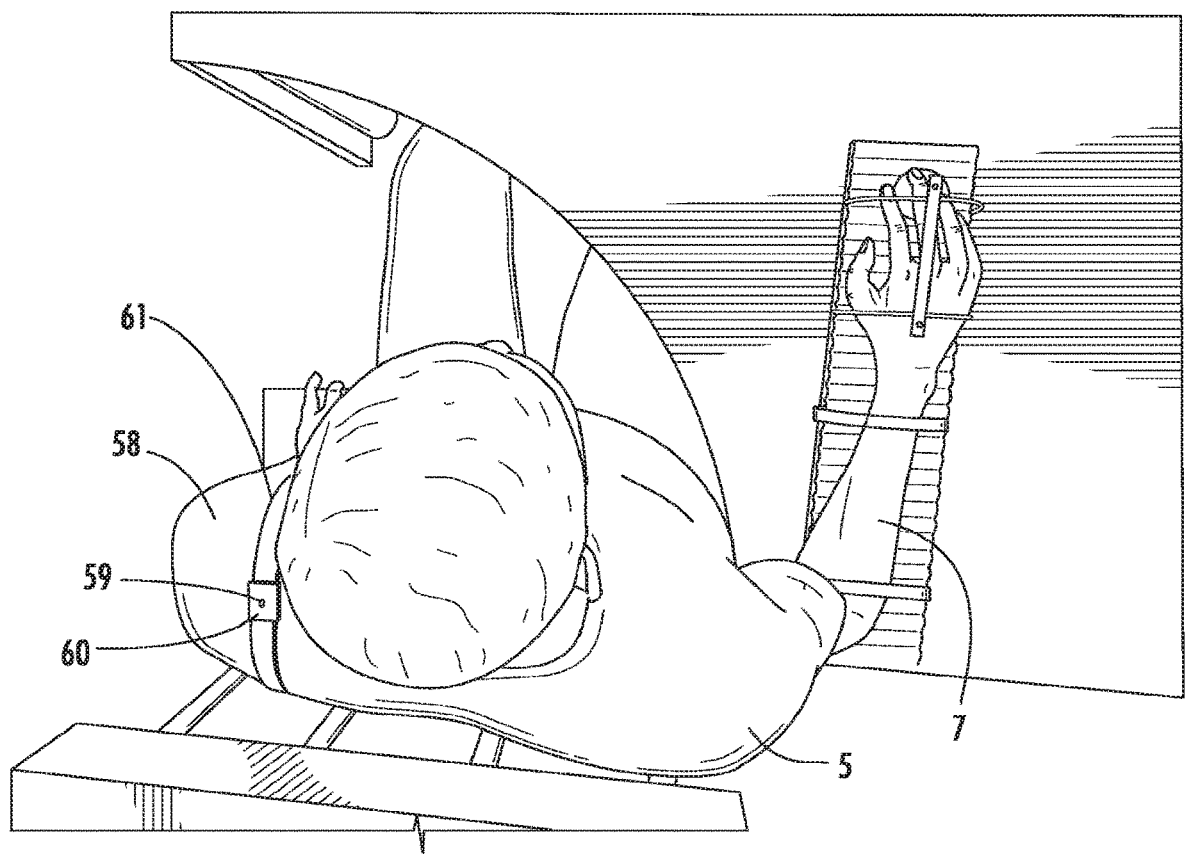
FIG. 10 is a view of the patient wearing a shoulder harness assembly used in the tilting rehabilitation table system.

FIG. 10 shows shoulder harness assembly 57 worn by patient 5 on shoulder 58 opposite to arm 7 being rehabilitated. Shoulder harness assembly 57 incorporates shoulder LED 59 wired to battery 60. Shoulder LED 59 is an infrared LED for providing data on compensatory movements of patient 5. Harness assembly 57 is formed of adjustable segments 61. Segments 61 are preferably formed of a hook and loop material, such as VELCRO®. Video camera 9 takes images of shoulder LED 59. Tracking software 18 running on computer 16 determines when patient 5 is doing undesirable compensatory leaning movements. Tracking software 18 can be adjusted by a therapist to be more sensitive, or less sensitive to leaning of patient 5.

Figure 11:
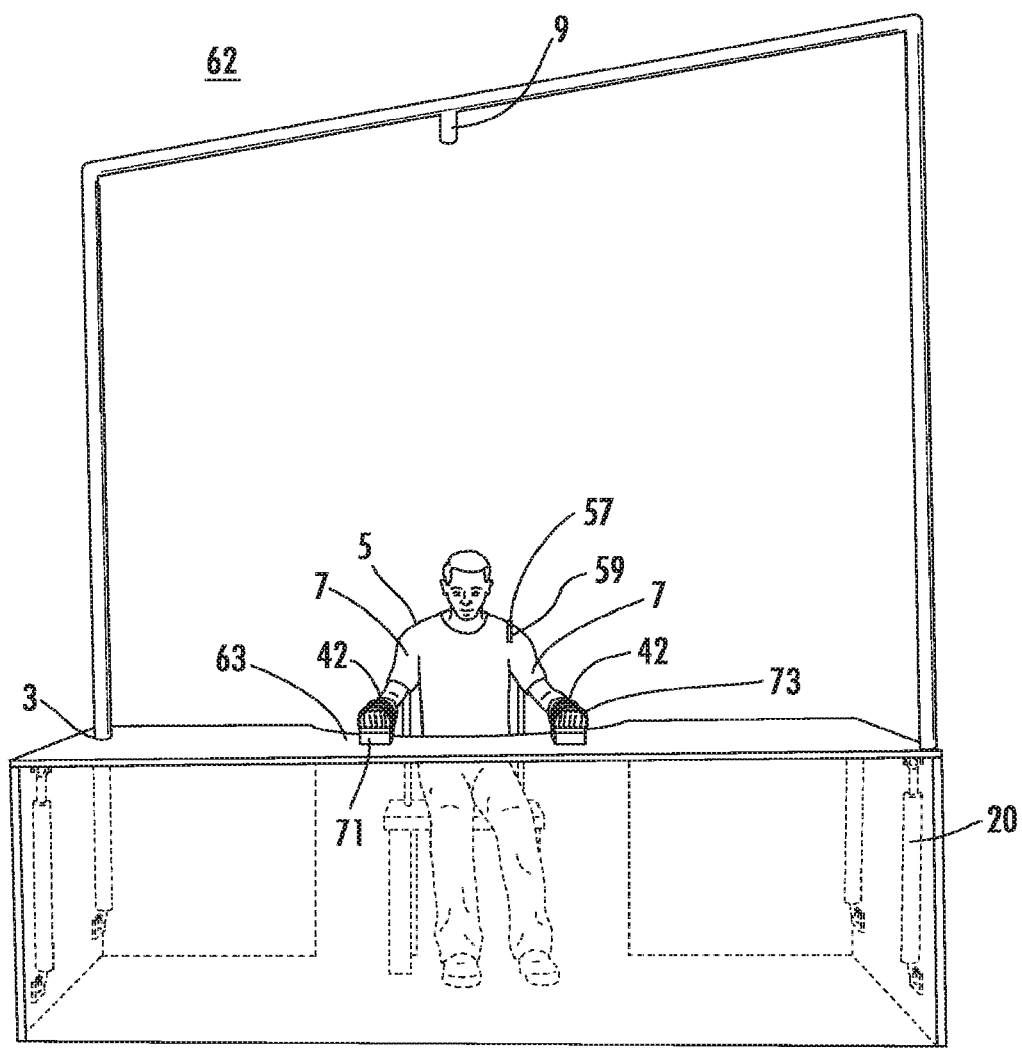
FIG. 11 is a schematic diagram of an alternate embodiment of the tilting table.

FIG. 11 illustrates an alternate embodiment of tilting table 62 for use with two forearm supports 25. Top surface 3 has a U-shape cutout 63 allowing patient 5 to be seated centrally to table axis 64. Patient 5 moves two arms 7 while supported by two low-friction forearm support assemblies 25. This allows training of both arms simultaneously, with benefits to recovery of patient 5. In one embodiment, patient 5 also wears one shoulder harness 57, as it is sufficient to detect the leaning of the shoulder opposite to the disabled arm 7. Video camera 9 views LEDs 42 on both forearm support assemblies 25, as well as LEDs 59 on one shoulder harness assembly 57. Forearm support assembly 25 is modified such that the number of infrared LEDs 42 differs between the two forearm support assemblies 25. For example three LEDs 42 will be on the left-arm forearm support 73, while the right-arm support 71 still has two LEDs 42 as previously described in FIG. 8. This allows tracking software 18 to differentiate between left arm and right arm movements. Tracking software 18 tracks two arms 7 in real time. Data from tracking software 18 is used by computer 16 to run two-arm exercise simulation 17. In this embodiment, the same type of actuators 20 as shown in FIG. 5, can be used in this embodiment. Preferably, four actuators 20 are used in this embodiment.

Figure 12:
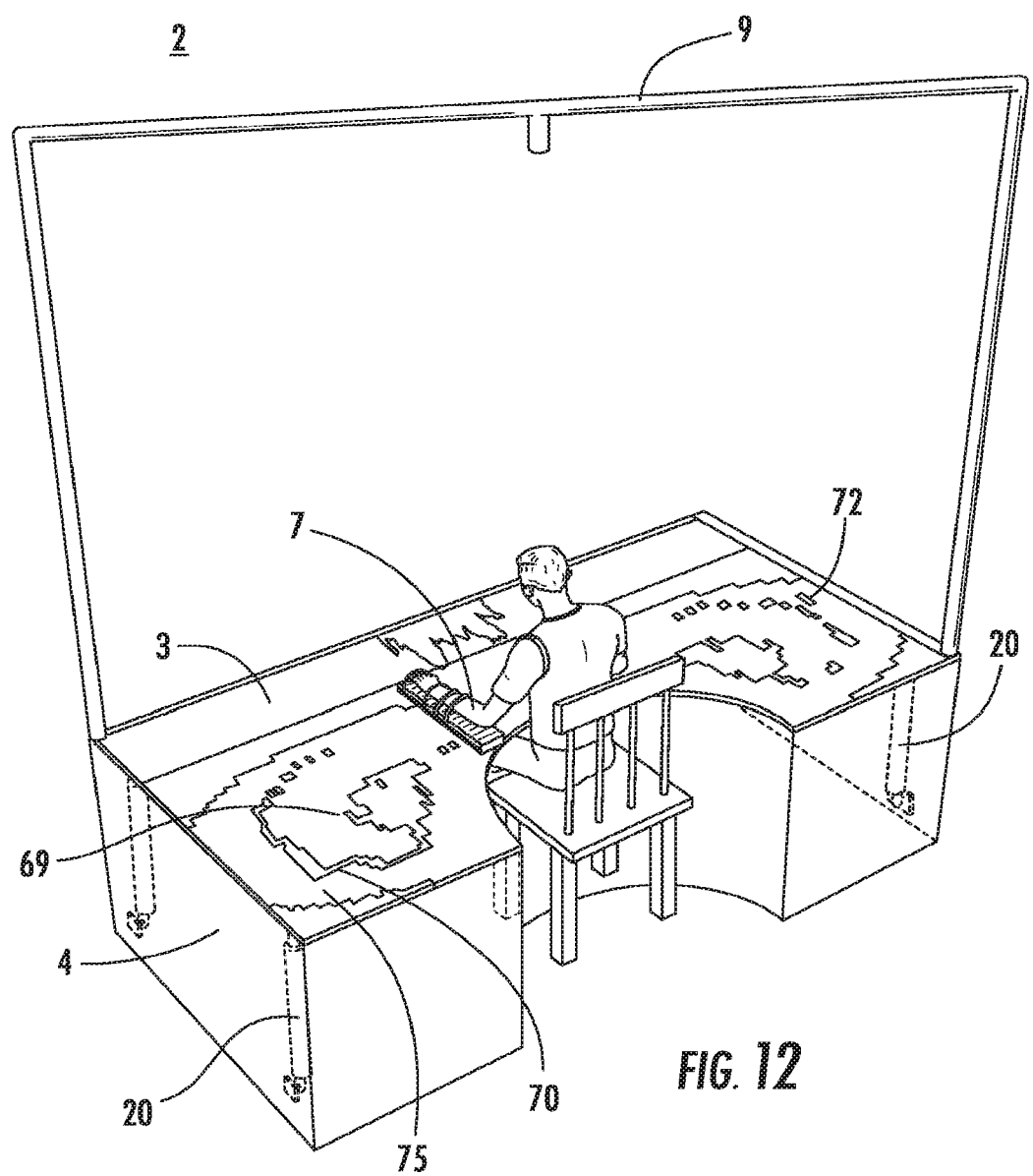
FIG. 12 is a schematic diagram of an alternate embodiment of the tilting table where top surface is a display.

FIG. 12 illustrates an alternate embodiment of tilting table 2. In this embodiment, top surface 3 is also display 69. For example, display 69 can be similar to commercially available thin organic LED (OLED) displays. In this embodiment, the tracking of forearm 7 may be performed by infrared camera 9, or through a touch-sensitive layer 70 incorporated in display 69. In this case the display 69 is a touch sensitive screen such as those available commercially. In case overhead camera 9 is used, forearm support assembly 25 is modified as shown in FIG. 11. Actuator assembly 20 can be connected to frame 72 bordering display 69 and to supporting surface 4. A low-friction transparent film 75 can be retrofitted to display 69, to prevent scratching by the forearm support assemblies 71 and 73 that sit on it.

Figure 13:
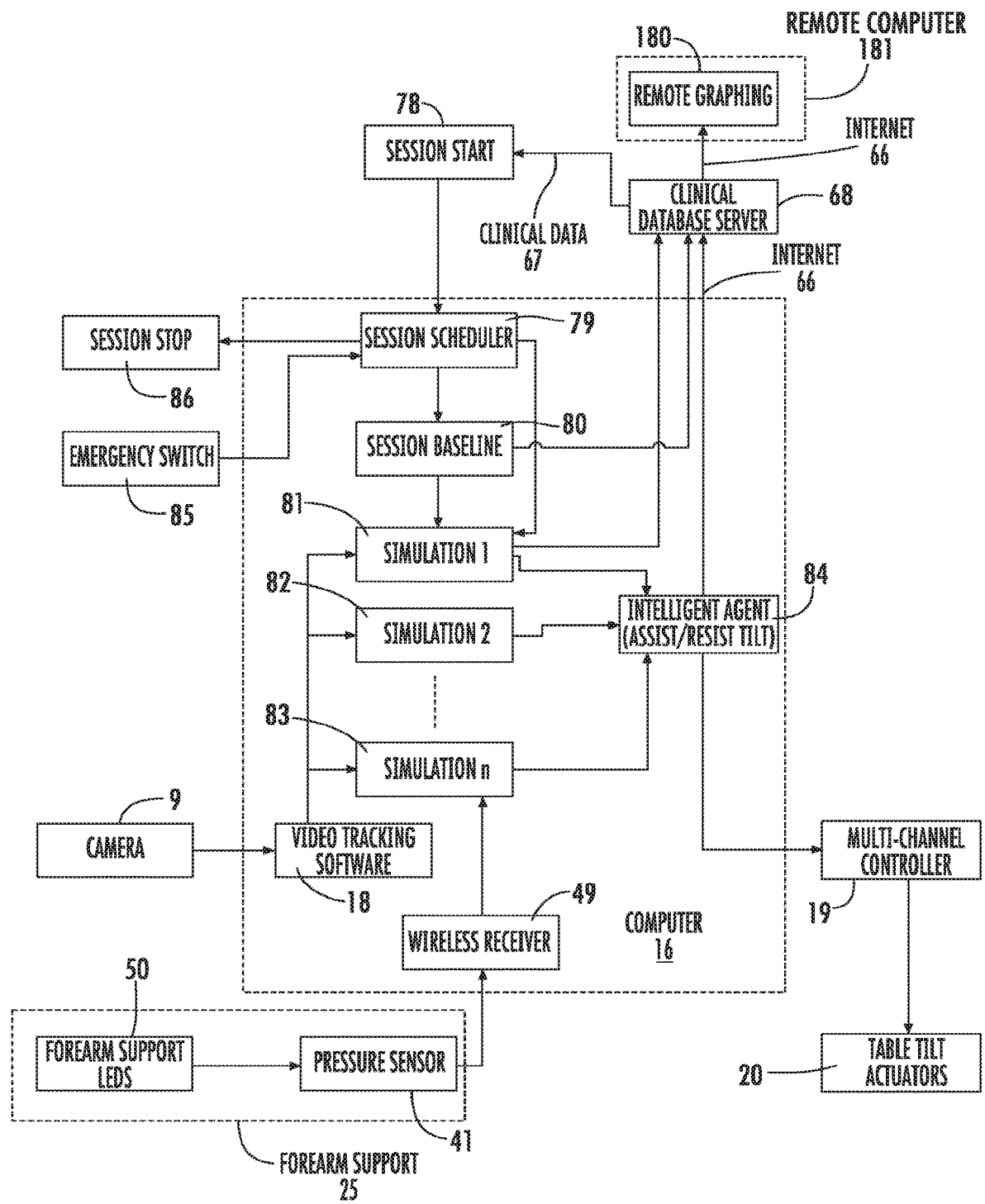
FIG. 13 is a system block diagram for the tilting rehabilitation table system.

A system block diagram for the tilting rehabilitation table system 1 is illustrated in FIG. 13. Each rehabilitation session starts with session start block 78. Session start block 78 loads the patient's ID and other clinical data 67 for arm 7 to be rehabilitated. Session start block 78 transfers control to the session scheduler block 79 which sets the structure of a rehabilitation session, for example, number, type and order of exercises, as well as the difficulty level settings. Session scheduler block 79 is structured such that it applies a customized treatment depending on progress of patient 5 (the order of the particular session being done out of the prescribed number of sessions). Session scheduler block 79 begins by starting session baseline 80 which measures the performance of patient 5 in that day. Session baseline 80 is stored transparently by clinical database server 68 and can be used to track progress of patient 5 over the sequence of rehabilitation sessions. Patient 5 progress can be graphed using remote graphing application 180 running on remote computer 181. It is envisioned that remote computer 181 communicates with clinical database server over Internet 66. Session baseline 80 is also used to fine-tune the "gains" of exercise simulation blocks 81, 82 and 83, such that in virtual reality movements are amplified and success assured even for very limited real arm 7 movements. Exercise simulation blocks 81, 82 and 83 can perform exercise simulation 17. Intelligent agent block 84 monitors the patient progress and can automatically vary tilt angle 15 to assist/resist movement. Intelligent agent block 84 can control actuators 20 through their controller 19 connected to computer 16 running exercise simulation blocks 81, 82 and 83. Actuators 20 provide data to exercise simulation blocks 81, 82 and 83 such that virtual table (not shown) in the scene mimics tilt of tilting table 2. Video camera 9 detects the position of LEDs 50 at the top of forearm support assembly 25 and sends the information to tracking software 18 run by computer 16. Tracking software 18 extracts arm position information and body leaning information and transmits this data to exercise simulation blocks 81, 82 and 83. This data is then used to animate in real time an avatar of the patient's hand(s) (not shown). Manual emergency switch 85, when pressed by attending therapist and/or patient 5 triggers an end to the rehabilitation session through software block 86.

Figure 14:
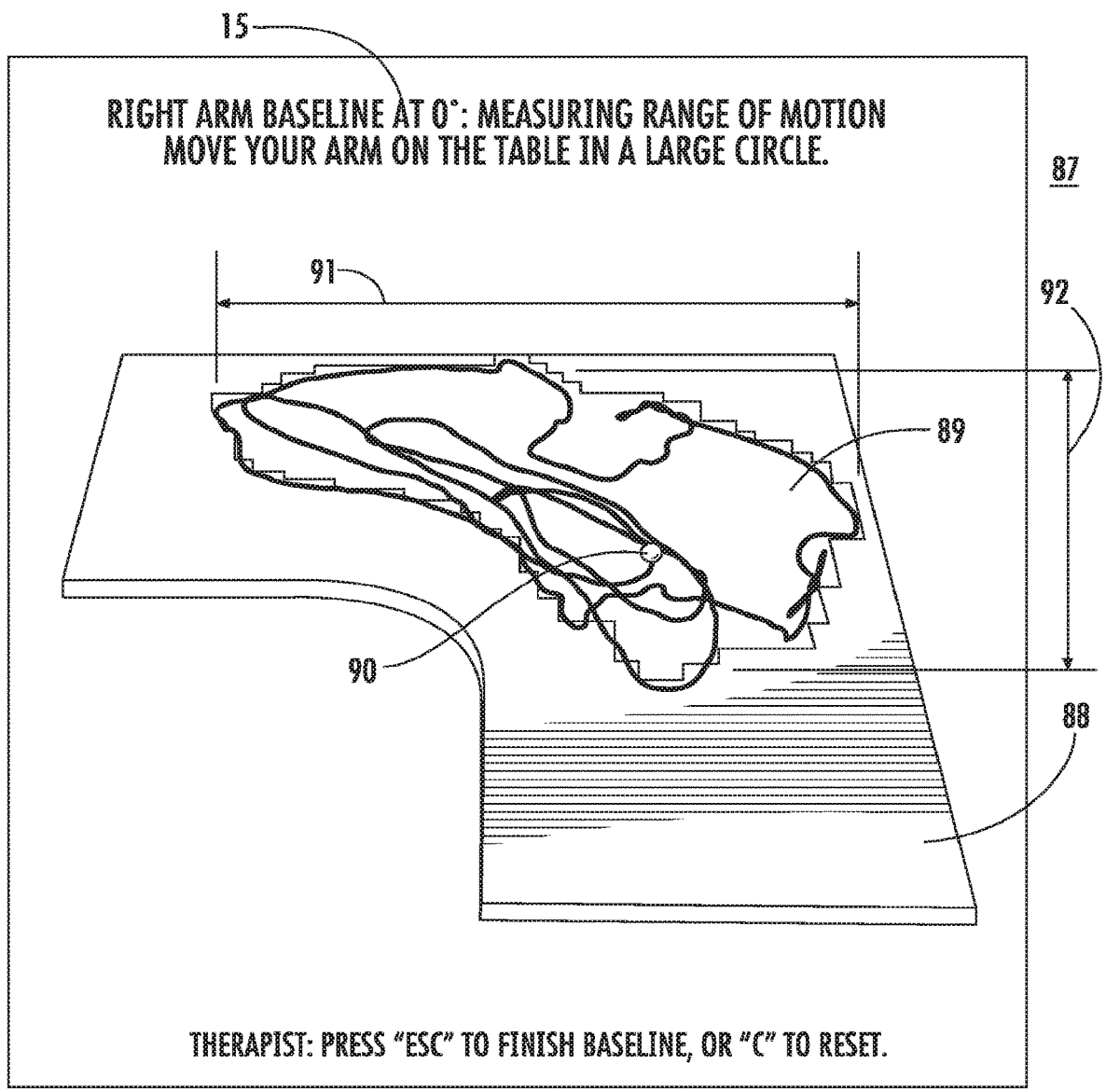
FIG. 14 is a schematic diagram of a patient baseline screen displayed by the tilting rehabilitation table system.

FIG. 14 illustrates an example of patient baseline screen 87 displayed in display 8 or on display 69. Patient 5 is asked to move the arm 7 in large circles to color virtual representation 88 of the rehabilitation table surface 3. The surface of colored area 89 increases with the movement of virtual sphere 90 which responds to the movements of forearm support assembly 25. Size and shape of colored area 89 are a measure of the ability of patient 5 that day. Extent of movement 91 in the left/right (horizontal) direction and extent of movement 92 in the in/out direction are used to adjust the rehabilitation exercise simulation blocks 81, 82 and 83. Baseline screen 87 also shows tilt angle 15 at which baseline 80 was taken.

Figure 15A:
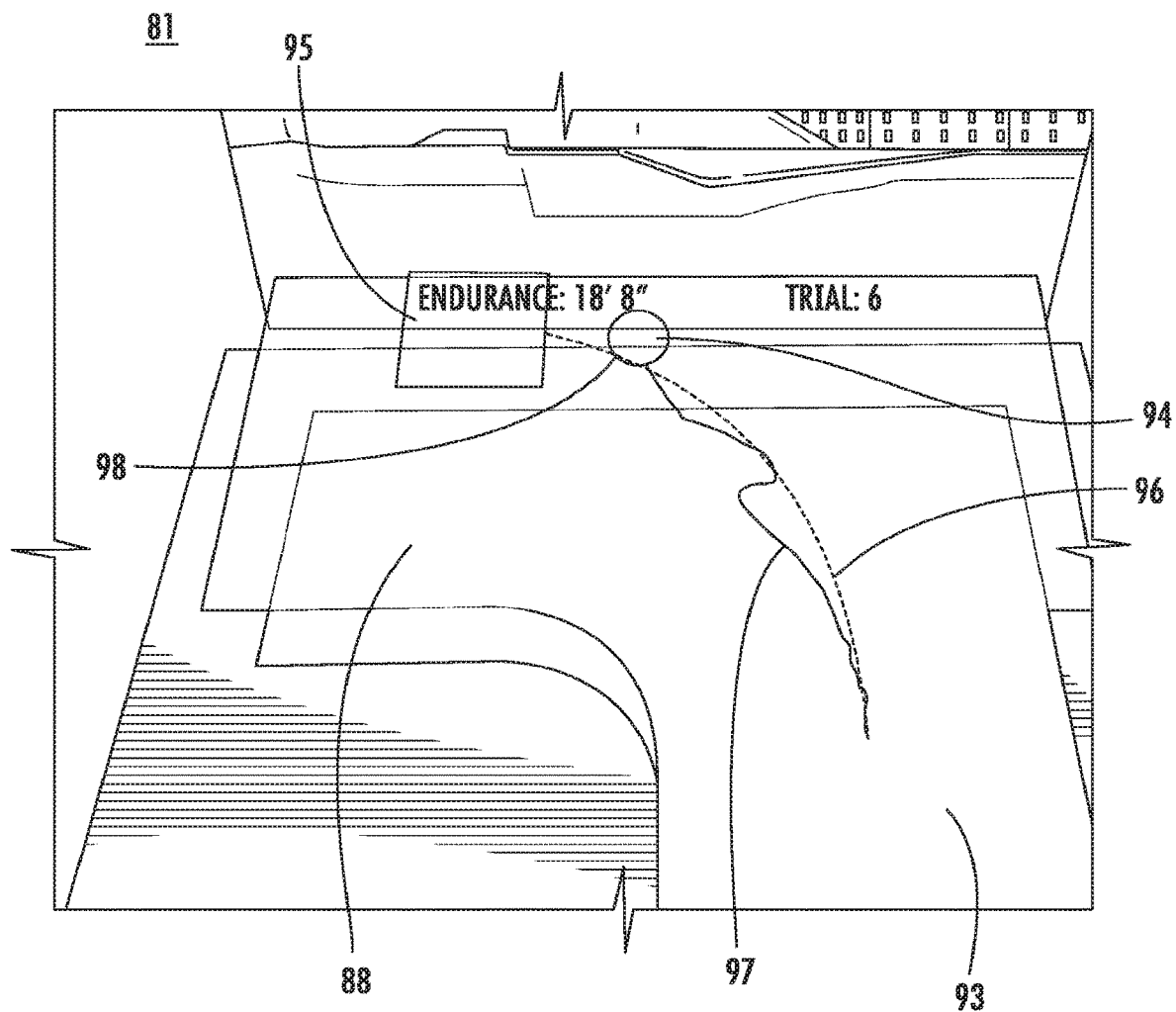
FIG. 15A is a schematic diagram of a virtual scene displayed by the tilting rehabilitation table system.

FIG. 15A shows an embodiment of rehabilitation exercise simulation block 81 with a virtual world representation having tilted table avatar 88. Virtual sphere 94 is shown on table surface 93 together with a virtual target rectangle 95. An ideal path between virtual sphere 94 and virtual target rectangle 95 is visualized by path shown as dotted line 96. The placement of virtual target rectangle 95 and virtual sphere 94 on table surface 88 is such that it requires patient 5 to move arm 7 close to extent of movement 91 and extent of movement 92 of baseline 87. Patient 5 is asked to pick up virtual sphere 94 with a semi-transparent hand avatar 98 and place it in virtual target rectangle area 95. In order to grasp virtual sphere 94, transparent hand avatar 98 has to overlap virtual sphere 94 and patient 5 squeezes compliant element 44 on forearm support assembly 25, as shown in FIG. 1. Real movement of patient 5 is tracked by video camera 9 and computer 16 shows a corresponding trace 97 on table surface 88.

Figure 15B:
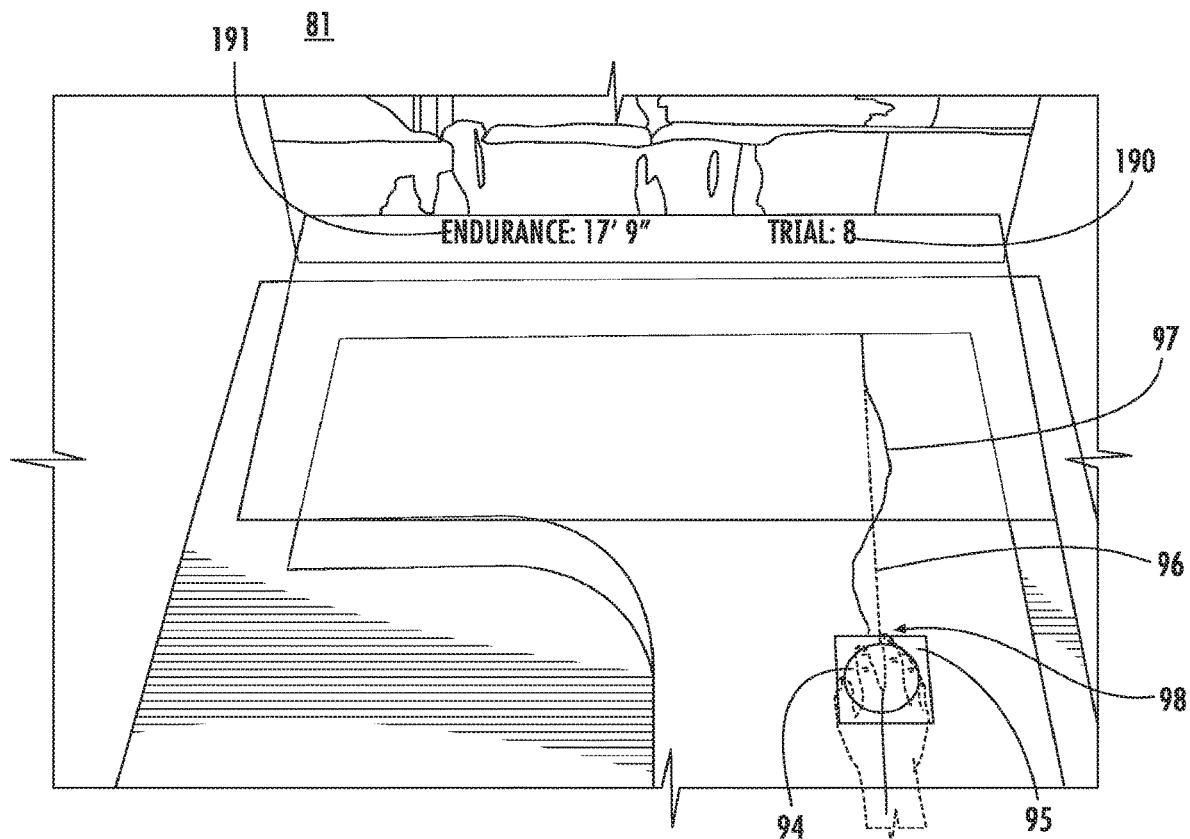
FIG. 15B is a schematic diagram of a virtual scene displayed by the tilting rehabilitation table system.

FIG. 15B shows an alternate embodiment of exercise simulation block 81 of the pick-and-place exercise in which ideal path 96 shown as a straight dotted line. This corresponds to in/out movements of arm 7. This process is repeated a number of times, with the trial (repetition) number 190 and the total arm movement (endurance) 191 corresponding to these repetitions being displayed in simulation 81. Other placements of virtual target rectangle 95 and virtual sphere 94 can be used with corresponding ideal path specifications 96. The difficulty exercise simulation block 81 such as a pick-and-place exercise, is varied by making virtual target rectangle 95 smaller and by requiring patient 5 to make more pick-and-place movements. For patient 5 capable of exerting finger forces 45, difficulty is further increased by elevating the threshold of finger grasping forces 45 detected by the forearm assembly 25 in FIG. 8 at which level corresponding hand avatar 98 can capture virtual sphere 94.

Figure 15C:
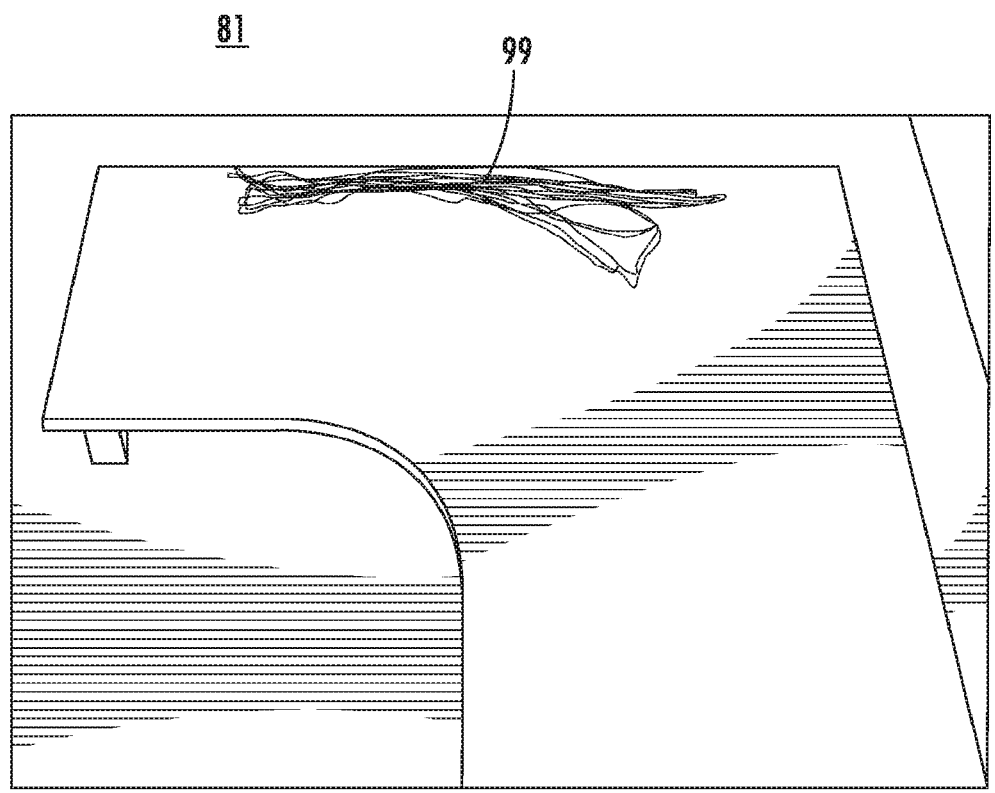
FIG. 15C is a schematic diagram of a virtual scene displayed by the tilting rehabilitation table system.

FIG. 15C shows bundle of traces 99 displayed by exercise simulation block 81 at the end of exercises after a number of pick-and-place movements were completed. In this embodiment, bundle of traces 99 corresponds to repeated pick-and-place movements of arm 7 in the left-right-left direction. The tightness of bundle of traces 99 is indicative of the motor control abilities that day for patient 5.

Figure 16A:
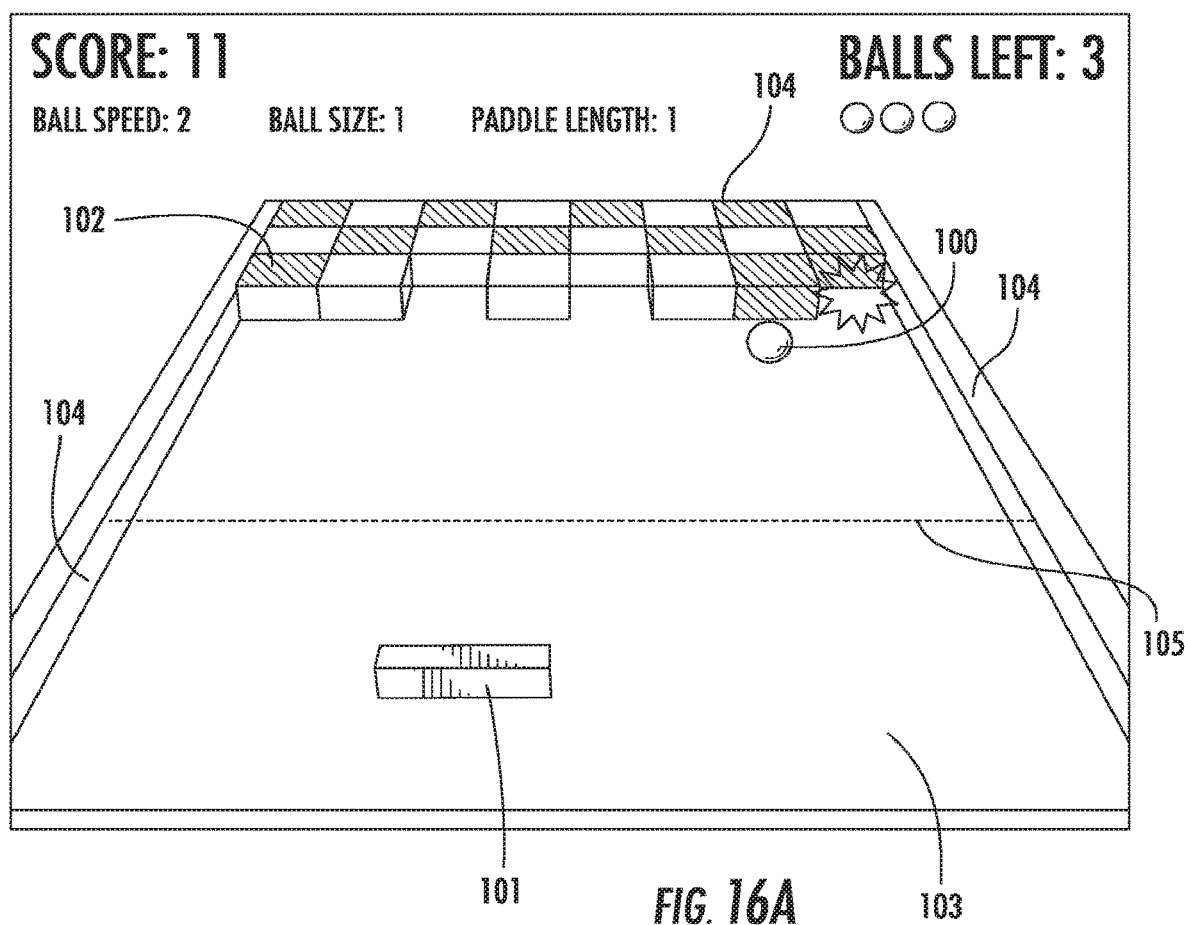
FIG. 16A is a schematic diagram of a virtual scene displayed by the tilting rehabilitation table system.

FIG. 16A shows an embodiment of exercise simulation block 82 referred to "Breakout 3D". This exercise depicts ball 100, paddle 101, and array of cubes 102, all located on play board 103. Paddle 101 is used to bounce ball 100 towards cubes 102 with one cube being destroyed for each bounce of ball 100 off of paddle 101. Ball 100 can bounce off of three sides 104 of play board 103, or off multiple cubes 102, but is lost if it misses paddle 101. In an alternate embodiment, paddle 101 can move mostly left-right, within the lower portion of play board 103, delineated by dashed line 105. The difficulty of exercise simulation block 82 is set by the number of available balls 100, the speed of balls 100, and the size of paddle 101. The higher the speed of ball 100, the smaller the size of paddle 101, and the fewer the number of available balls 100, the harder the Breakout 3D of exercise simulation block 82 game is. The goal of the Breakout 3D exercise simulation block 82 is to destroy all cubes 102 with the available number of balls 100. The Breakout 3D of exercise simulation block 82 is designed to improve hand-eye coordination and cognitive anticipatory strategies of patient 5.

Figure 16B:
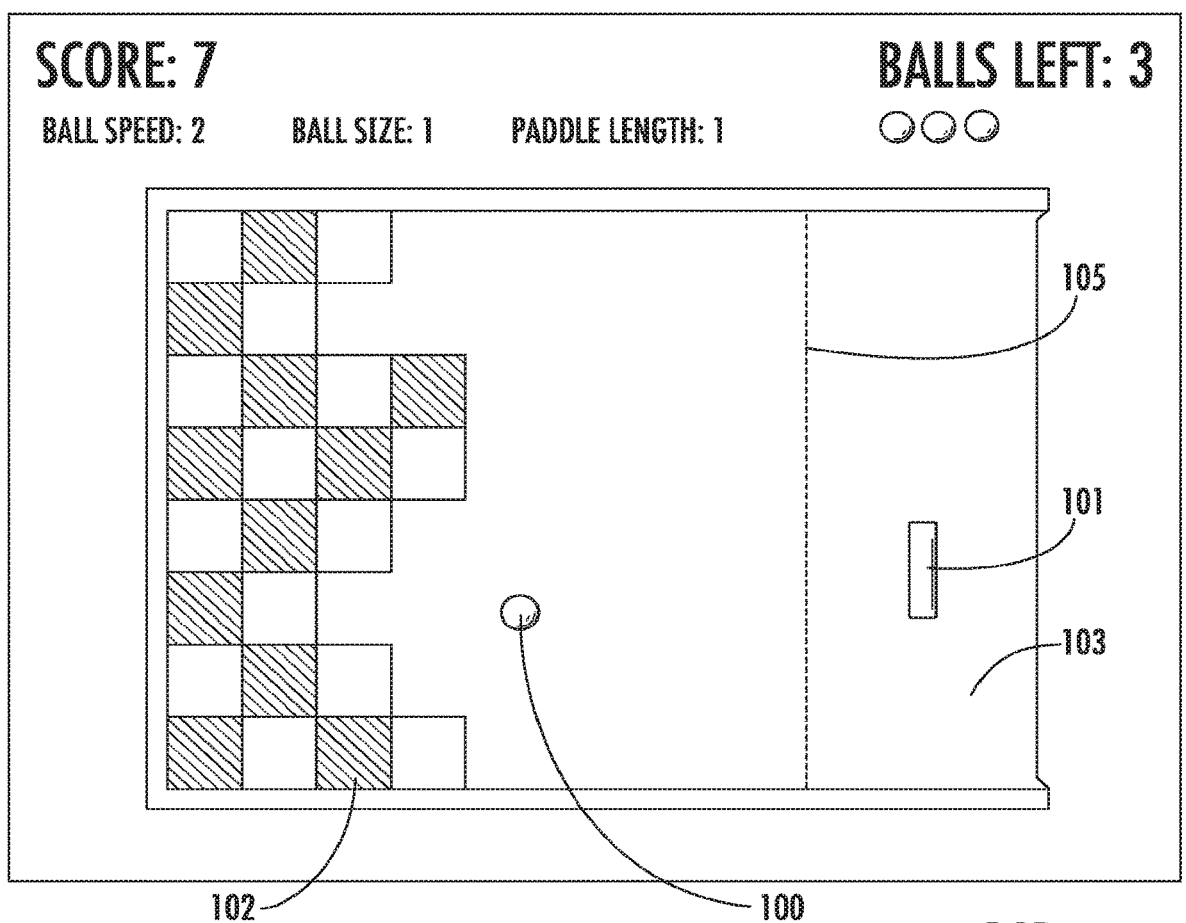
FIG. 16B is a schematic diagram of a virtual scene displayed by the tilting rehabilitation table system.

FIG. 16B is another embodiment of the Breakout 3D of exercise simulation block 82, in which board 103 is rotated to show array of cubes 102 to one side of the scene. In this example paddle 101 moves mostly vertically in the scene, within the area to the right of dotted line 105, requiring corresponding in-out-in movements of arm 7.

Figure 17:
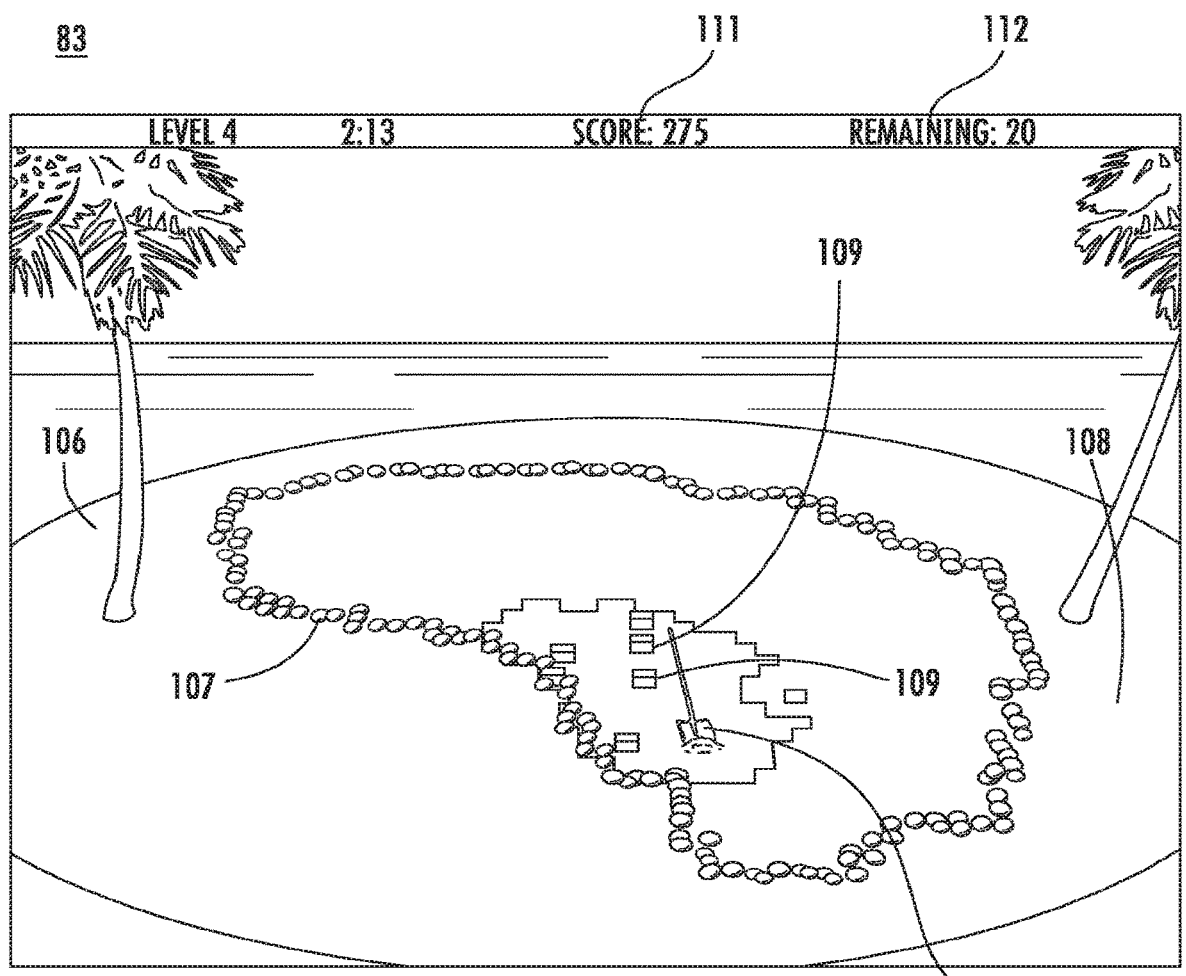
FIG. 17 is a schematic diagram of a virtual scene displayed by the tilting rehabilitation table system.

FIG. 17 is an embodiment of exercise simulation block 83 called "Treasure Hunt". The scene depicts deserted island 106 with line of stones 107 on top of virtual sand 108. The shape of line of stones 107 replicates the shape of baseline surface colored area 89. There are a number of virtual treasures chests 109 inside sand 108 surrounded by line of stones 107. Patient 5 controls virtual shovel 110 with which to remove sand 108 covering treasure chests 109. Every time a new treasure chest 109 is found score 111 displayed in the scene is increased. In order to find a new treasure chest 109 shovel 110 has to be moved in sand 108 that overlaps treasure chest 109. If tracking software 18 detects leaning of patient 5 treasure chest 109 is not revealed even if shovel 110 is in the correct position and score 111 is not increased. At higher level of difficulty, a sand storm occurs. Part of the already uncovered treasure chests 109 are covered again by sand 108 requiring more movement of arm 7 of patient 5 arm 7 to uncover treasure chest 109 again. The Treasure Hunt exercise simulation block 83 is timed and remaining time 112 is displayed at the top of the scene. Patient 5 attempts to uncover all of treasure chests 109 in the allowed amount of time 112. This exercise is aimed at increasing arm endurance of patient 5. In other embodiments, other simulation exercises can be played by patient 5.

Figure 18A:
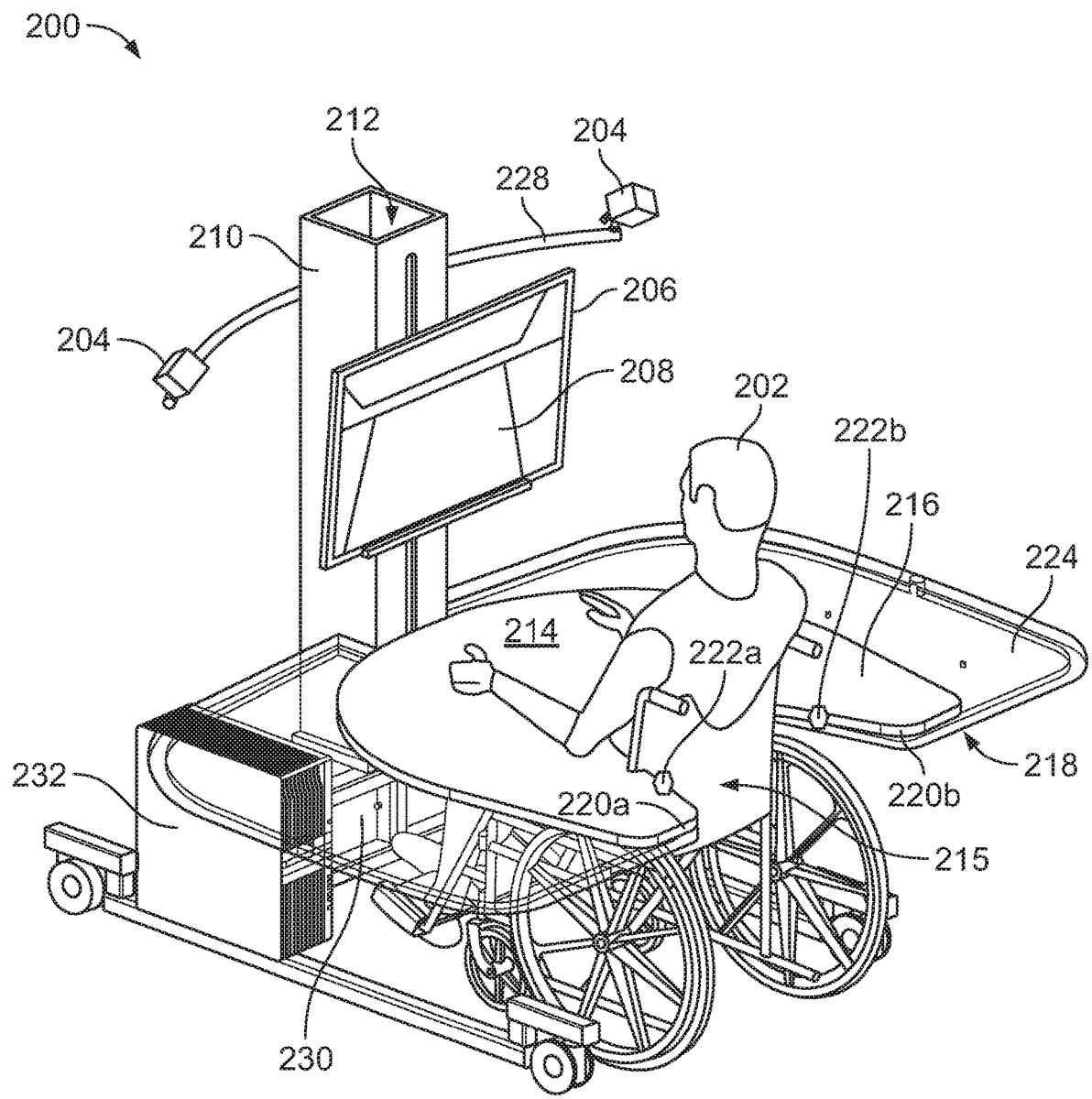
FIG. 18A is a rear view schematic diagram of another aspect of the tilting rehabilitation table system.
Figure 18B:
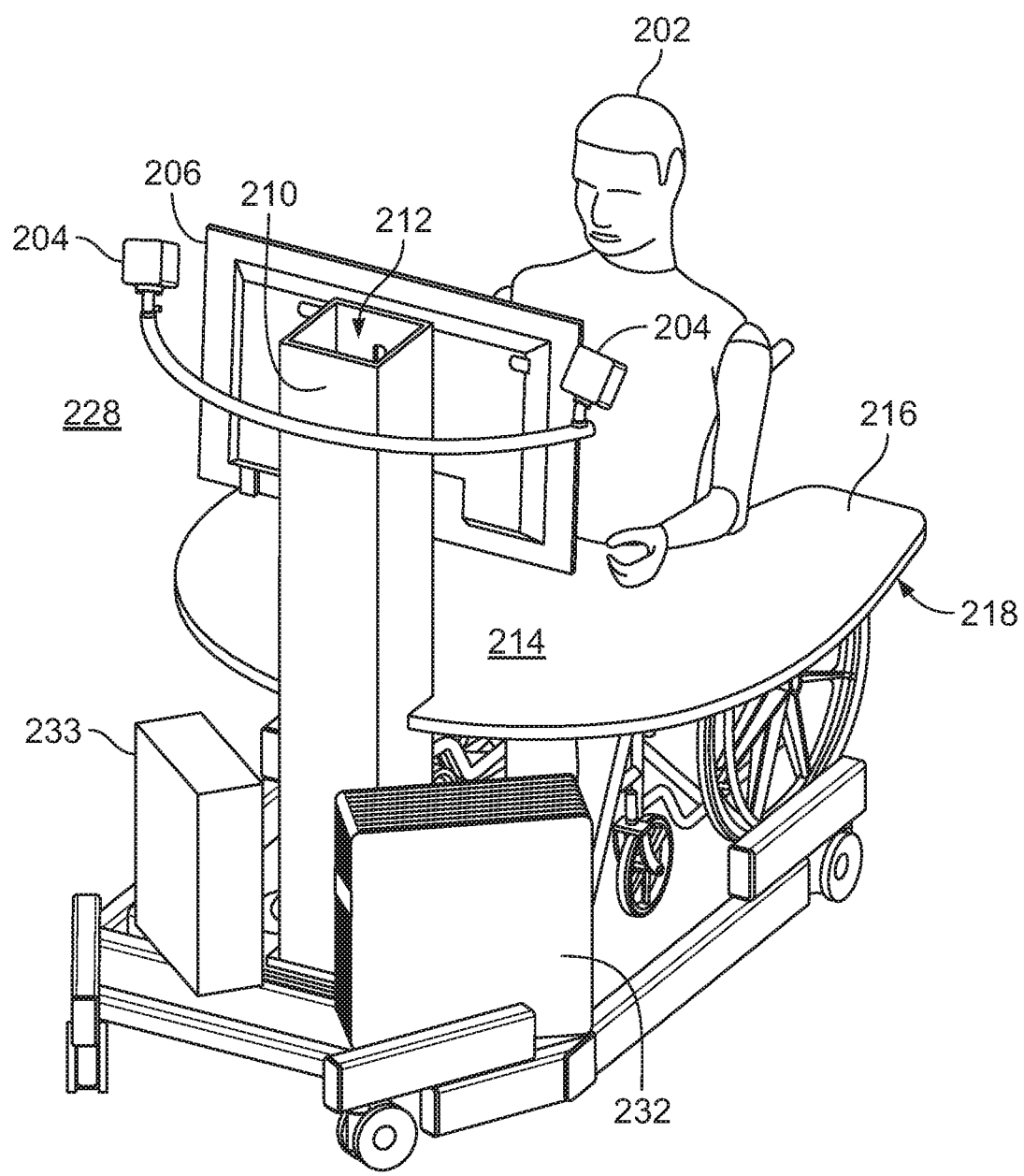
FIG. 18B is a front view schematic diagram of another aspect of the tilting rehabilitation table system.

FIGS. 18A and 18B are respectively rear and front view schematic diagrams of another aspect of the tilting rehabilitation table system 200. The tilting and lifting rehabilitation table system 200 includes a infrared emitter system 204, a display 206, a hollow vertical support 210, a tilting and lifting table 214, a base 230, a computer 232 and a control box 233.

The tilting and lifting table 214 has a top surface 216 and an underside surface 218. The tilting and lifting table 214 may have a shape matching the perimeter of a person's arm span reaching forward and sweeping back, with a parabolic entry 215 to accommodate a patient 202 when seated at the tilting and lifting table 214 of the tilting rehabilitation table system 200. The parabolic entry 215 accommodates a torso of the patient 202. In addition, the parabolic entry 215 may also accommodate a manually operated (e.g., a wheel chair) or a power-driven device designed for use by a patient 202 with a mobile disability. The parabolic entry 215 is placed such that the tilting axis 3000 of the top surface 216 passes through the torso of patient 202.

A sensor 222a may be positioned on an interior wall 220a of the parabolic entry 215 and another sensor 222b may be positioned on an interior wall 220b of the parabolic entry 215. The sensors 222a and 222b may be infrared or LED sensors or the like. The sensors 222a and 222b may detect whether a patient 202 is properly seated at the tilting and lifting table 214 of the tilting rehabilitation table system 200 by detecting whether a beam between the sensors 222a and 222b is interrupted when the patient 202 is seated. In addition, at least one sensor 226 (not illustrated) may be positioned on the underside surface 218 of the tilting and lifting table 214. The sensor 226 (not illustrated) may be also be an infrared or LED sensor or the like. The sensor 226 may detect a position of the legs of the patient 202 via an infrared beam such that the tilting and lifting table 214 does not immediately contact the legs of the patient 202.

The tilting and lifting table 214 may be symmetrical, light weight and have a low-friction top surface. For example, the tilting and lifting table 214 may be carbon fiber or another durable and light weight material wherein the top surface 216 has a low-friction coating. Suitable low-friction coatings may include TEFLON® sheets or Formica or other such materials.

To use the tilting rehabilitation table system 200, the patient 202 rests at least one arm to be rehabilitated on the top surface 216 of the tilting and lifting table 214 wherein the at least one arm is positioned in a low-friction forearm controller (not illustrated) to allow for pronation and supination forearm rotation. The low-friction underside of the forearm controller minimizes friction between the at least one arm of the patient 202 and the top surface 216 of the tilting and lifting table 214 as the patient 202 moves the forearm controller over the top surface 216. For example, the low-friction forearm controller may be a controller as disclosed in U.S. patent application Ser. No. 15/669,952. It is appreciated that the tilting and lifting rehabilitation table system 200 may benefit a patient 202 with at least one weak arm such as a patient 202 who has survived a stroke. The tilting and lifting rehabilitation system 200 may also benefit a patient 202 having chronic upper body pain (e.g., nerve pain), a traumatic brain injury (e.g., a brain concussion) and/or arthritis (e.g., rheumatoid arthritis), or any patient in need of physical and/or mental rehabilitation.

A size of the tilting and lifting table 214 may meet at least the ninetieth percentile of an average adult's reach when seated at the tilting and lifting table 214 of the tilting rehabilitation table system 200. Accordingly, the tilting rehabilitation table system 200 requires less clinical space for operation, transport when stowed (e.g., the system 200 may fit through a doorway) and storage when stowed. For example, tilting and lifting table 214 has reduced size than tilting table 224 of other aspects of the tilting and lifting rehabilitation table system.

The patient 202 exercises via the forearm controller while viewing a graphic display 208 on a display 206. The display 206 may be a medical grade monitor or television (e.g., a high-definition television (HDTV)), have any suitable dimensions, large or small, such as a television of 43" diagonal, or larger, or smaller, and include at least one speaker to provide sounds associated with the graphic display 208. The display 206 is mounted on a vertical support 210 such that the patient 202 may view the graphic display 208 on the display 206 when seated at the tilting and lifting table 214 even when the tilting and lifting table 214 is positioned at an angle. The vertical support 210 may be rigid, hollow and houses a lift and tilt mechanism 212 for modifying a position of the tilting and lifting table 214 relative to the patient 202. Infrared emitters 204 are also mounted on the vertical support 210, or on the TV, via a rigid U-shaped support 228, or other suitable mounting means, wherein the infrared emitters 204 are fixed on the support 228 and positioned at or above the display 206. The infrared emitters 204 may also be positioned to be even with sides of the display 206. The infrared emitters 204 may be HTC VIVE infrared emitters, which are commercially available. Alternatively, the infrared emitters 204 may be conventional digital cameras having infrared filters attached to the lenses thereof.

The arrangement of the infrared emitters 204 and display 206 relative to the patient 202 allows the infrared emitters 204 to be directed to the tilting and lifting table 214 and patient 202 simultaneously. Infrared receivers/detectors may be mounted on the top surface 216 of the tilting and lifting table 214 to calibrate the infrared emitters 204 and to locate movement and position on the patient's arms during use. The support bar 228 is mounted to the vertical support 210 such that the support bar 228 maintains the same relative orientation regardless of a tilt angle of the top surface 216, thereby making re-calibration of the infrared emitters 204 unnecessary if a tilt angle of the tilting and lifting table 214 changes during a rehabilitation session. The vertical support 210 is positioned on a top frame 234 of the base 230 such that the legs of the patient 202 may be accommodated under the tilting and lifting table 214 without interference from a base of the vertical support 210.

Computer 232 may be enclosed in a box for safety and protection, while a control box 233 (FIG. 18b) houses at least one electronic controller to control actuators located in vertical support 210. Computer 232 renders an exercise simulation displayed as a graphic display 208 on the display 206. The exercise simulation may be an animated sequence or a virtual reality sequence. For example, the exercise simulation 17 could be at least one game. Games may be a plurality of simulations 17, may differ and may be sequenced to form an integrative rehabilitation session wherein the cognitive, motor and emotive aspects of a patient 202 are treated simultaneously. The brain of a patient 202 may be engaged by playing the games with at least one arm and hand.

The computer 232 may be a multi-core PC workstation. To render graphics quickly, it is appreciated that computer 232 may incorporate a graphics card (not shown). Computer 232 receives an input from the forearm supports based on signals from the infrared emitters 204. As mentioned above with reference to FIG. 2, the computer 232 may execute tracking software and communicate with a electronic controller positioned inside the control box 233, wherein the controller activates actuators to tilt the tilting and lifting table 214 during a rehabilitative session. The computer 232 may also be connected to the Internet and upload clinical data based on the rehabilitative session to a remote clinical database server. It is appreciated that such clinical data may be an automatically-generated session report. For example, when a patient 202 participates in a rehabilitative session, the computer may store and upload clinical data including but not limited to specific games played, duration, performance, scores, error rates, cognitive area trained and a number of movement repetitions by the arms and fingers of a patient 202. The computer 232 may also compose a rehabilitative session report that may be presented locally on the display 206 and/or transmitted to a remote clinician.

Accordingly, the tilting and lifting rehabilitation table system 200 provides advantages over conventional systems and methods relating to an elevated intensity of a rehabilitation session and lower costs of a rehabilitation session based on the automated collection, compilation and transmission of clinical data regarding the rehabilitation session. Further advantages of the system 200 is that the system 200 allows for training both arms simultaneously, which is associated with a higher level of brain training and physical exercise. Yet another advantage of the system 200 is increased patient 202 safety. The system 200 is passive wherein actuators are not connected directly to the arms of a patient 202, unlike rehabilitation robots which are active elements.

Figure 19:
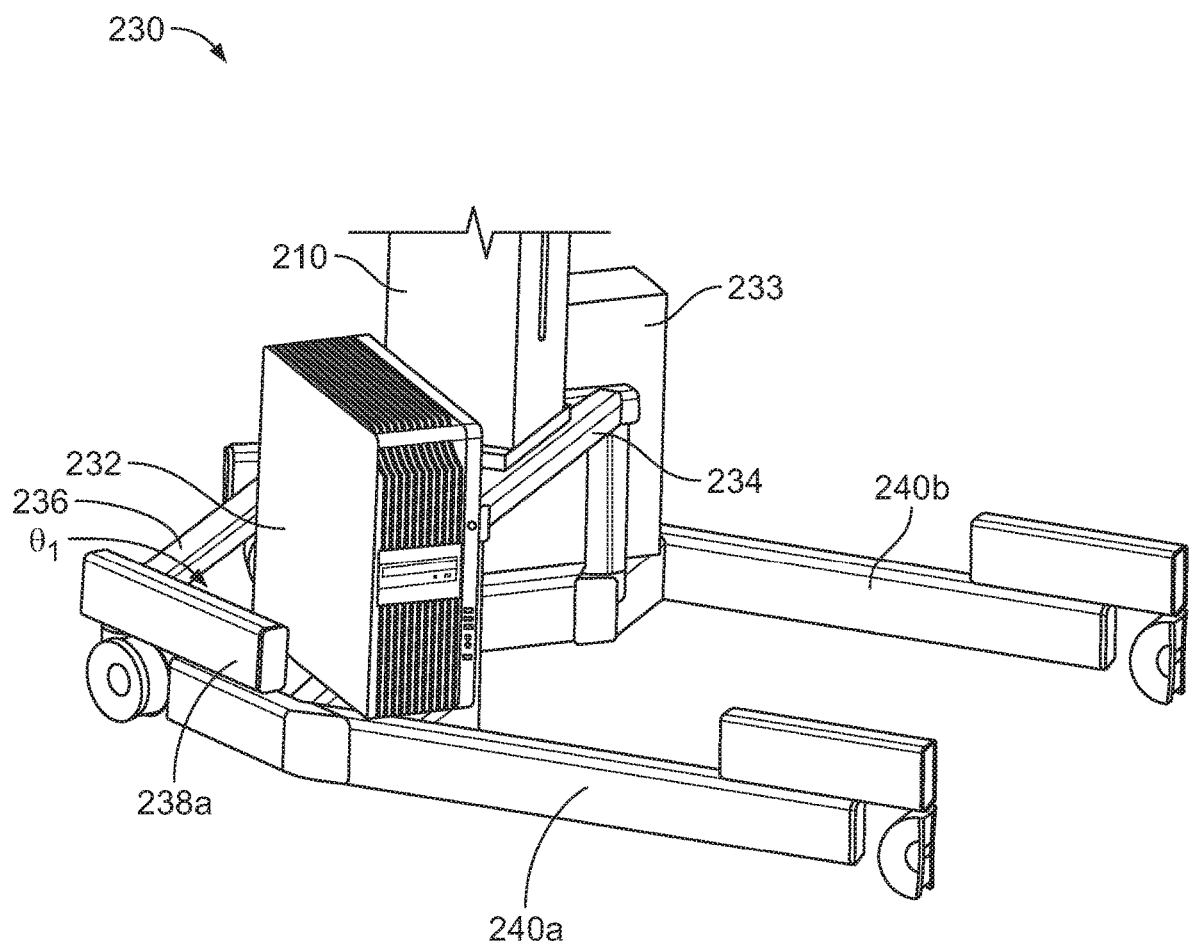
FIG. 19 is a schematic diagram of a base of the tilting rehabilitation table system of FIG. 18.

FIG. 19 is a schematic diagram of the base 230 of the tilting and lifting rehabilitation table system 200. The base 230 includes a top frame 234, a rear frame 236, a first side frame 238a and a second side frame 238b (not illustrated) wherein a first leg frame 240a extends from the first side frame 238a and a second leg frame 240b extends from the second side frame 238b. The vertical support 210 is positioned on a top surface of the top frame 234 such that the legs of the patient 202 may be accommodated under the tilting and lifting table 214 without interference from a base of the vertical support 210. The first side frame 238a and the second side frame 238b, respectively extend from the rear frame 236 at obtuse angles $\theta_1$ and $\theta_2$ (not illustrated) such that a distance between the first leg frame 240a and the second leg frame 240b is greater than a length of the rear frame 236. Accordingly, the base 230 may accommodate a base portion (or foot support mechanism) of a manually operated (e.g., a wheel chair) or a power-driven device designed for use by a patient 202 with a mobile disability.

Figure 20:
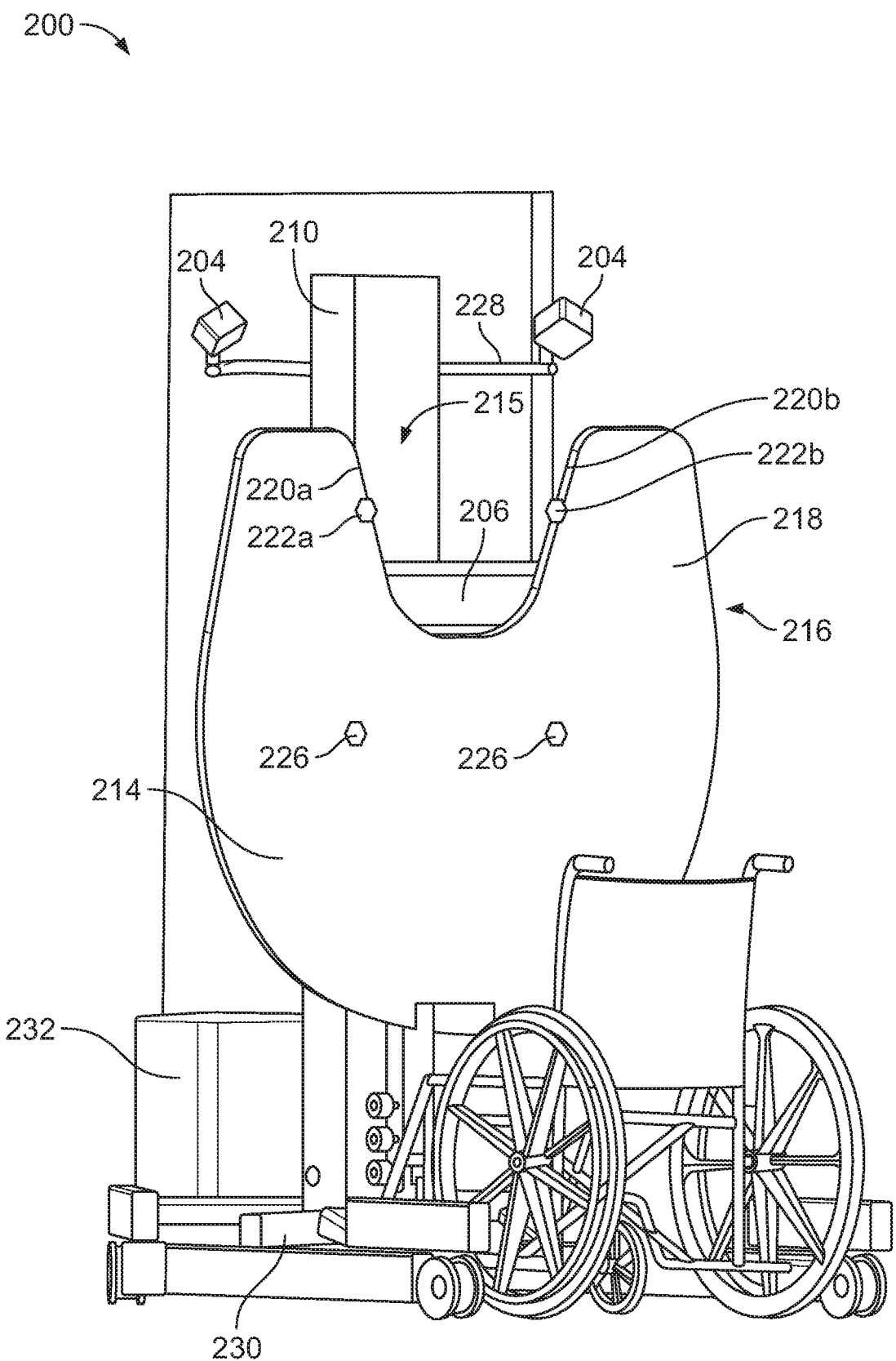
FIG. 20 is a schematic diagram of the tilting rehabilitation table system of FIG. 18 in a stowed position for storage and/or transport.

FIG. 20 is a schematic diagram of the tilting and lifting rehabilitation table system of FIG. 18 in a stowed position for storage and/or transport. As mentioned above in reference to FIG. 18, a size of the tilting and lifting table 214 may meet at least the ninetieth percentile of an average adult's reach when seated at the tilting and lifting table 214 of the tilting and lifting rehabilitation table system 200. Accordingly, the tilting and lifting rehabilitation table system 200 requires less clinical space for operation, transport when stowed (e.g., the system 200 may fit through a doorway) and storage when stowed. For example, tilting and lifting table 214 is smaller than tilting table 224 of another embodiment of the tilting rehabilitation table system.

Figure 21:
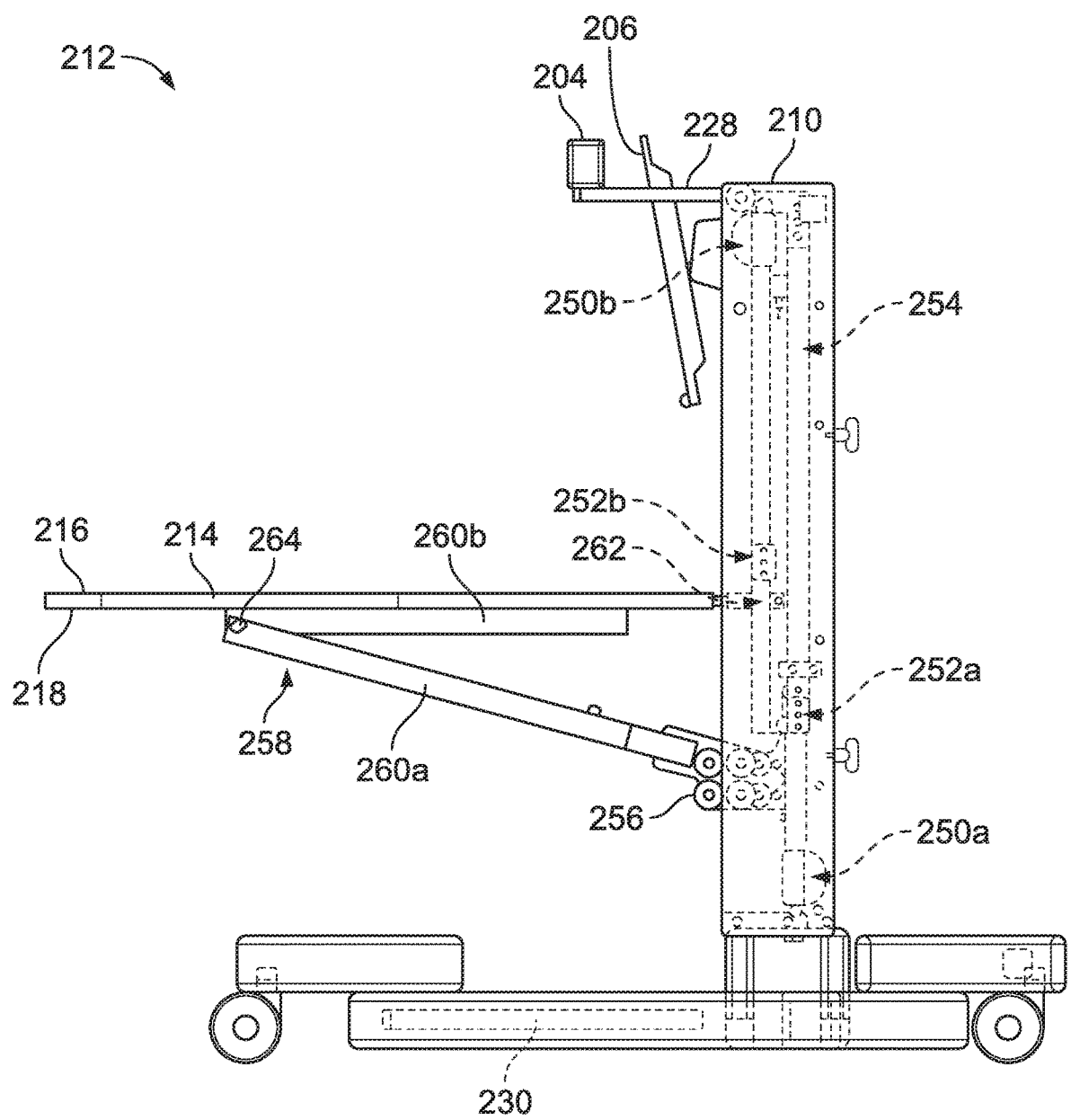
FIG. 21 is a schematic diagram of a lift and tilt mechanism of the tilting rehabilitation table system of FIG. 18.

FIG. 21 is a schematic diagram of a lift and tilt mechanism 212 of the tilting and lifting rehabilitation table system 200 of FIG. 18. The lift and tilt mechanism 212 includes a first actuator 250*a* coupled to a first vertical shuttle 252*a*, a second actuator 250*b* coupled to a second vertical shuttle 252*b*, a vertical linkage system 254, a rolling assembly 256, a lateral linkage system 258 including a first support 260*a* and a second support 260*b* and a slit-pinion mechanism 262. The vertical support 210 houses the first actuator 250*a*, the first vertical shuttle 252*a*, the second actuator 250*b* and the second vertical shuttle 252*b*, the vertical linkage system 254 and the slit-pinion mechanism 262.

A height of the tilting and lifting table 214 may be modified by the first actuator 250*a* in combination with the rolling assembly 256 An angle of the tilting and lifting table 214 may be modified by the second actuator 250*b* in combination with the slit-pinion mechanism 262. The first actuator 250*a* and the second actuator 250*b* may be linear electrical actuators. For example, the first actuator 250*a* may be a Progressive Automations PA-18_10 linear actuator and the second actuator 250*b* may be a Progressive Automations PA-18-30 linear actuator. A control box 233 (FIG. 18*b*) positioned on the base 230 houses electronics that control each of the first actuator 250*a* and the second actuator 250*b*. For example, a controller controls the first actuator 250*a* and the second actuator 250*b* based on received commands from the computer 232 when executing an exercise simulation. The controller may be a commercially available multi-channel micro-controller or another commercially available conventional controller. In addition, a first independent string potentiometer (not shown) measures a position of the first actuator 250*a*. A second independent string potentiometer measures a position of the second actuator 250*b*. The combination of inputs from the first and the second string potentiometers provides feedback to the controller to enable accurate control of each of the first actuator 250*a* and the second actuator 250*b*. The first string potentiometer is unwound by the linear movement of the first actuator 250*a* and the second string potentiometer is unwound by the linear movement of the second actuator 250*b*.

Figure 22:
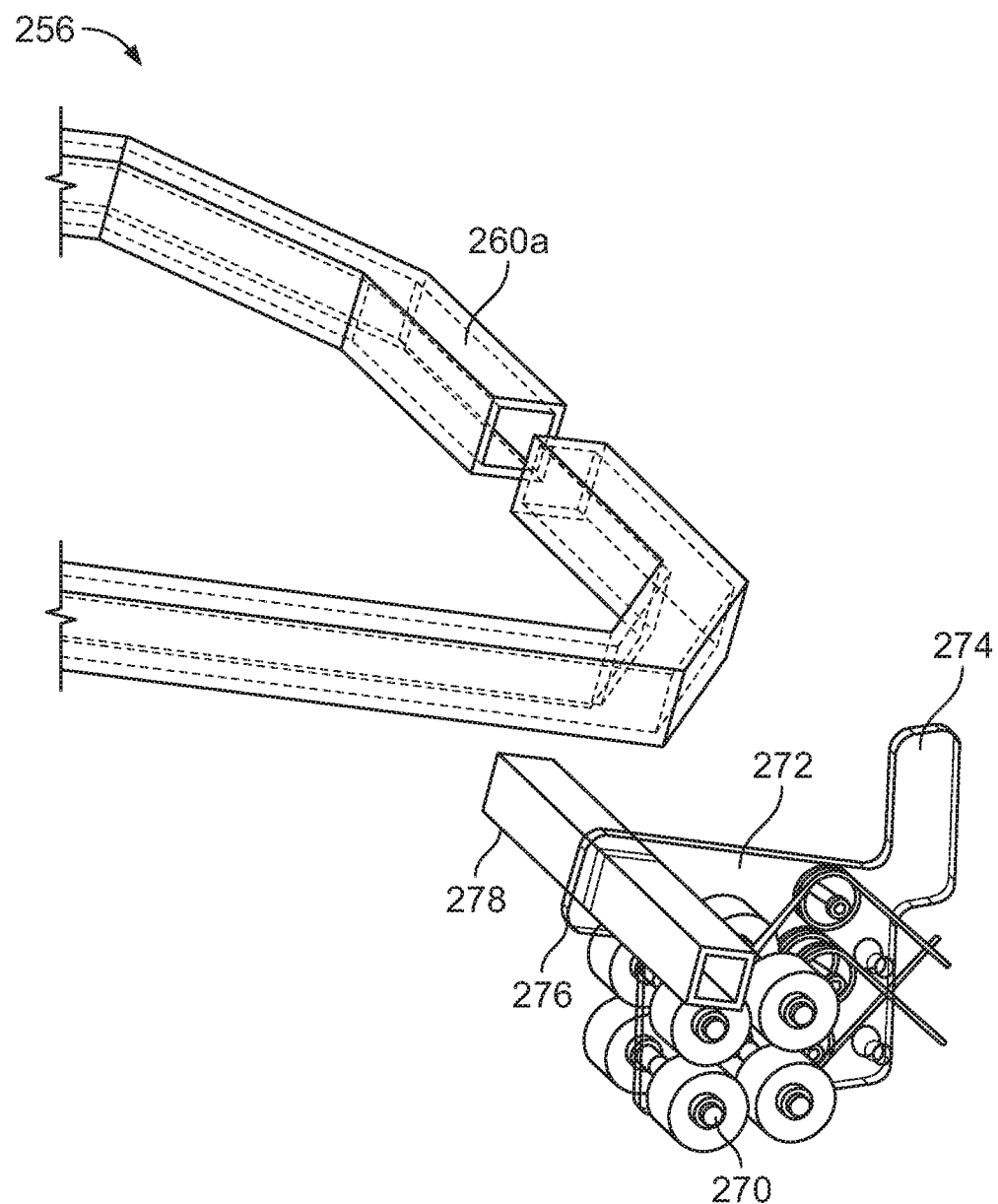
FIG. 22 is a schematic diagram of a rolling assembly of the lift and tilt mechanism of FIG. 21.

FIG. 22 is a schematic diagram of the rolling assembly 256 of the lift and tilt mechanism 212 of FIG. 21. The first actuator 250*a* has an anchor point coupled to the first vertical shuttle 252*a* and performs lift actuation to modify a height of the tilting and lifting table 214. Modifying a height of the tilting and lifting table 214 provides for accommodating varying body types of patients seated at the tilting and lifting table 214.

The rolling assembly 256 includes a plurality of plastic roller pairs 270, a metal plate 272 having an extension 274 and an opening 276, and a mating bar 278 positioned within the opening 276. The plurality of plastic roller pairs 270 are configured such that respective rollers of a pair are positioned on opposite sides of the metal plate 272. In addition, half of the plurality of plastic roller pairs 270 may be positioned within the vertical support 210 and half of the plurality of plastic roller pairs 270 may be positioned outside of the vertical support 210. The plurality of plastic roller pairs 270 may include plastic rollers similar to those known in the art (e.g., roller blade rollers). It is envisioned that such plastic rollers reduce the noise generated when lifting or lowering the table 214. The extension 274 couples the rolling assembly 256 to the first vertical shuttle 252*a* and the opening 276 couples the rolling assembly 256 to the lateral linkage system 258. Specifically, the mating bar 278, positioned within the opening 276, may be positioned within the first support 260*a* to couple the rolling assembly 256 to the first support 260*a* of the lateral linkage system 258. The first actuator 250*a* and first vertical shuttle 252*a* in combination with the rolling assembly 256 may modify the height of the tilting and lifting table 214 with minimal noise and/or vibration. It is appreciated that the plurality of plastic roller pairs 270 may be vibration dampeners and motion guides.

Figure 23:
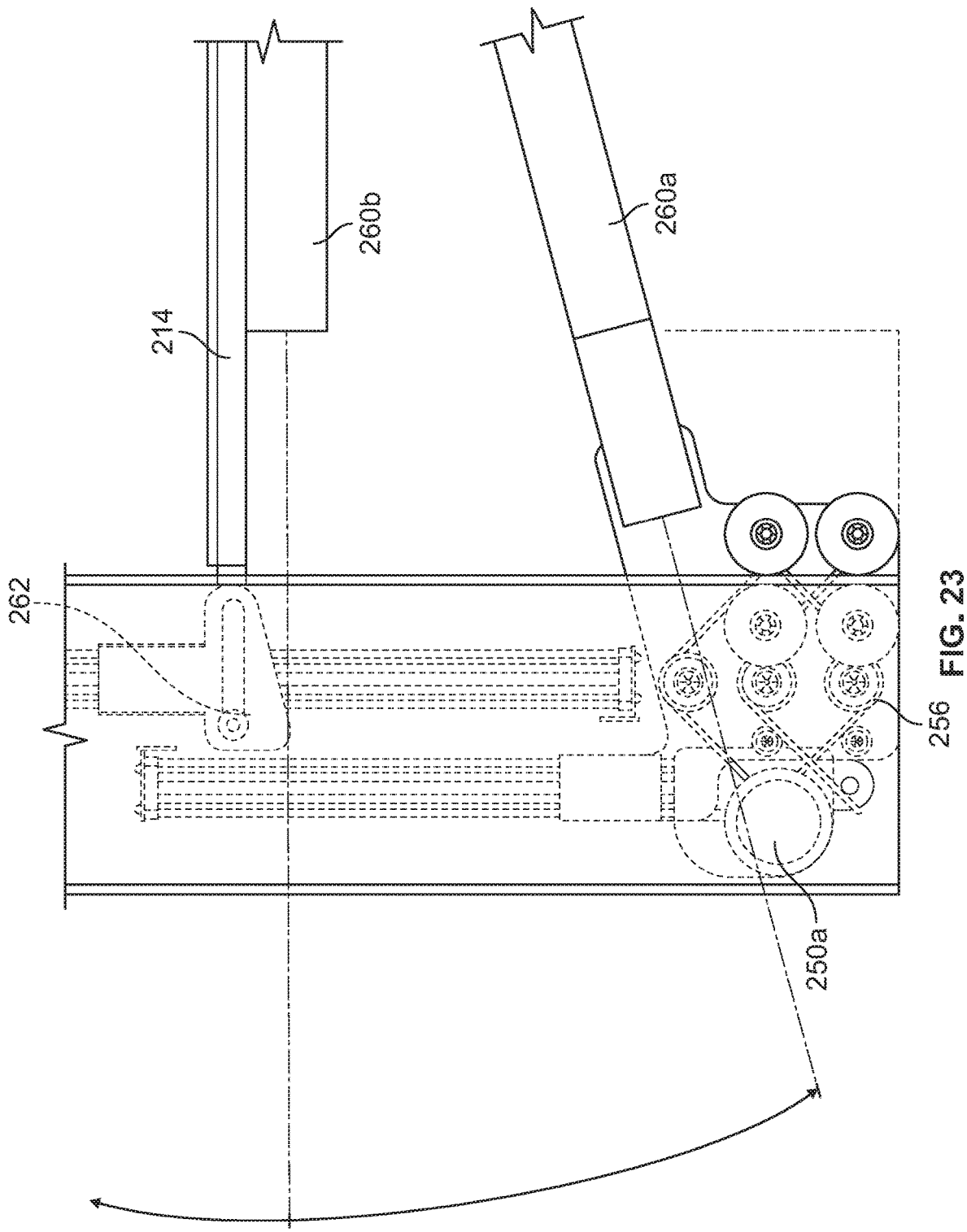
FIG. 23 is a schematic diagram of a slit-pinion mechanism of the lift and tilt mechanism of FIG. 21.

FIG. 23 is a schematic diagram of a slit-pinion mechanism 262 of the lift and tilt mechanism of FIG. 21. The second actuator 250*b* has an anchor point coupled to the second vertical shuttle 252*b* and performs tilt actuation to modify an angle of the tilting and lifting table 214. The slit-pinion mechanism 262 couples the second actuator 250*b* and second vertical shuttle 252*b* to the tilting and lifting table 214. The slit-pinion mechanism 262 provides for a rotary tilting movement of the tilting and lifting table 214 in comparison to the linear and vertical movement of the second actuator 250*b* and the second vertical shuttle 252*b*. Modifying an angle of the tilting and lifting table 214 modulates gravity acting on the arms of a patient 202. For example, tilting the tilting and lifting table 214 down facilitates movement of the arms of the patient 202 away from a trunk of the patient 202. Alternatively, tilting the tilting and lifting table 214 up resists the movement of the arms of the patient 202 away from the trunk of the patient 202.

Figure 24:
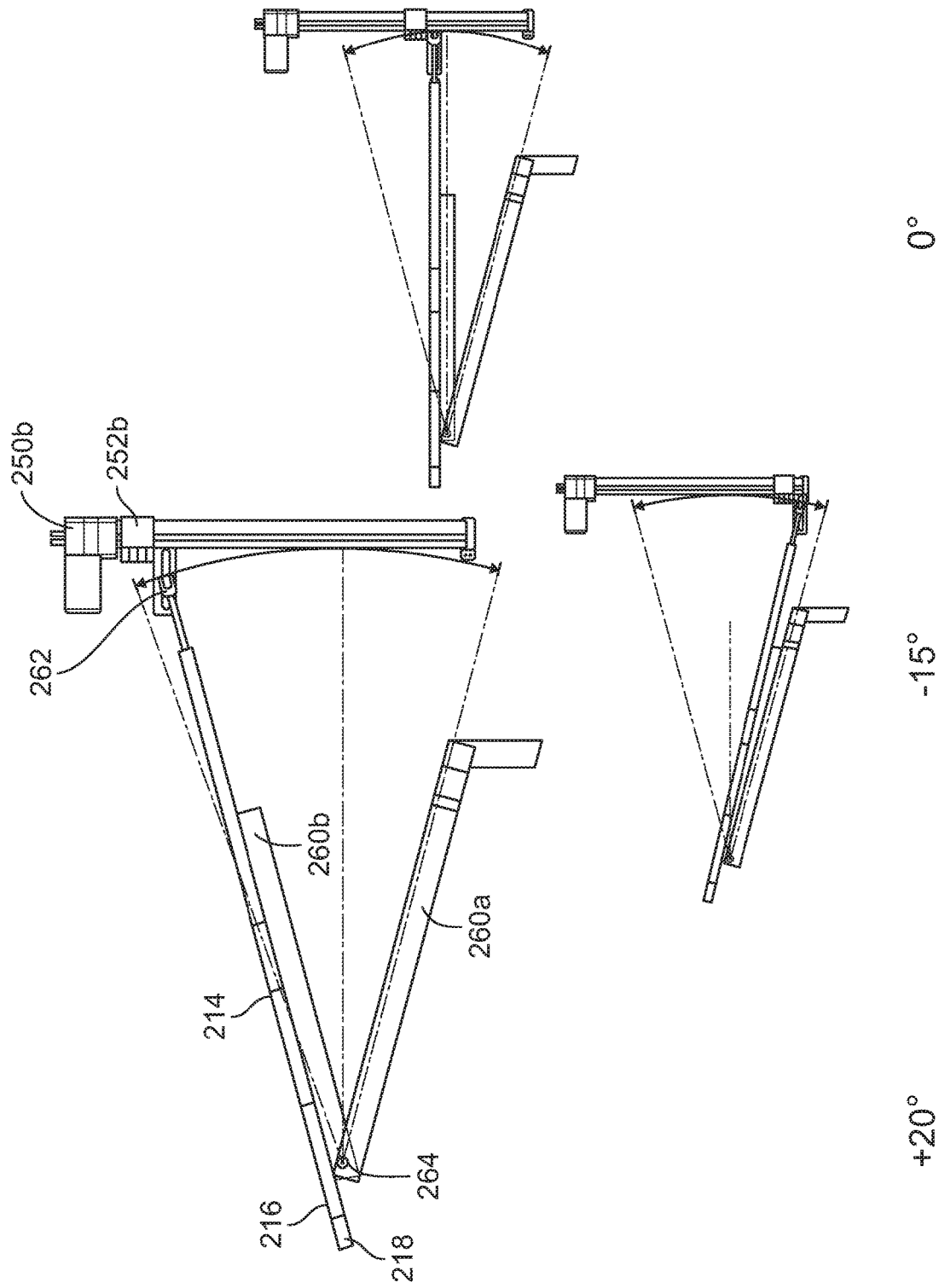
FIG. 24 is a schematic diagram of an angle adjustment range of the lift and tilt mechanism of FIG. 21.

FIG. 24 is a schematic diagram of an angle adjustment range of the lift and tilt mechanism 212 of FIG. 21. The lateral linkage system 258 includes a first support 260*a* coupled to the roller assembly 256 and a second support 260*b* coupled to the underside surface 218 of the tilting and lifting table 214 wherein the first support 260*a* and the second support 260*b* are coupled together by a rotary joint 264. In addition, the slit-pinion mechanism 262 couples the second actuator 250*b* and second vertical shuttle 252*b* to the tilting and lifting table 214. As such, the combination of the second actuator 250*b* and the second vertical shuttle 252*b*, the lateral linkage system 258 and the slit-pinion mechanism 262 provides for modifying an angle of the tilting and lifting table 214. For example, in one embodiment, the tilting and lifting rehabilitation table system 200 may utilize twenty-four inches of a thirty inch effective stroke span of the second actuator 250*b* which provides for a +20° to −15° angle adjustment range and adjustable difficulty levels for a patient 202. In addition, the second actuator 250*a* and second vertical shuttle 252*b* are coupled to the first actuator 250*a* and first vertical shuttle 252*a* via a linkage system 254. The linkage system 254 provides for modifying a height of the tilting and lifting table 214 without modifying an angle of the same.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the present disclosure.

What is claimed is:

1. A system for rehabilitation comprising:
a tilting table configured to be movable at a tilt angle in at least one degree of freedom, the tilting table having a low-friction top surface;
a forearm support configured to receive a forearm of a user, the forearm support being movable on, but not coupled to, the low-friction top surface of the tilting table;
an animated or virtual reality sequence forming an exercise simulation being displayed on a display coupled to a vertical support and positioned above the tilting table; and
a tracking device configured to track movements of the forearm support upon interaction of the user with the exercise simulation, wherein
the tracking device includes at least one infrared emitter and tracking software to track an output from at least one position sensor, the tracking device measuring the movements of the forearm support on the top surface of the tilting table, and
the at least one infrared emitter is coupled to the vertical support via a support bar and positioned to be above or even with the display such that the at least one position sensor tracks the movements of the forearm interaction regardless of the tilt angle of the tilting table.

2. The system for rehabilitation of claim 1, wherein the tilting table has a U-shape and includes a parabolic entry to accommodate a torso of the user when seated at the tilting table.

3. The system for rehabilitation of claim 2, wherein at least one safety mechanism is positioned on an underside of the tilting table, the at least one safety mechanism being configured to detect a proximity of knees and legs of the user when seated at the tilting table.

4. The system for rehabilitation of claim 2, wherein a first sensor is positioned on a first interior wall of the parabolic entry and a second sensor is positioned on a second interior wall of the parabolic entry, the first interior wall opposing the second interior wall, such that the first sensor and the second sensor are configured to determine whether the user is seated at the tilting table by detecting whether the user has interfered with a light beam between the first sensor and the second sensor.

5. The system for rehabilitation of claim 1, further comprising a first base wherein the first base includes
a forward frame and a rear frame, the forward frame being adjacent to the rear frame; and
a first side frame and a second side frame,
wherein
a first leg frame extends from the first side frame and a second leg frame extends from the second side frame,
the first side frame and the second side frame respectively extend from the rear frame at obtuse angles such that a distance between the first leg frame and the second leg frame is greater than a length of the rear frame, and
the vertical support is positioned on a top surface of the forward frame such that legs of the user may be accommodated under the tilting table without interference from a second base of the vertical support.

6. The system for rehabilitation of claim 1, further comprising
a first actuator coupled to a first vertical shuttle, the first actuator configured to control a height of the tilting table;
a second actuator coupled to a second vertical shuttle, the second actuator configured to control the tilt angle of the tilting table; and
a lateral linkage system including
a first support having a first end and a second end, the first end being coupled to the first vertical shuttle, and
a second support coupled to an underside surface of the tilting table and having a first end and a second end, wherein the second end of the first support and the second end of the second support are coupled together by a rotary joint.

7. The system for rehabilitation of claim 6, further comprising
a roller assembly including a plurality of roller pairs, a first end and a second end, the first end of the roller assembly being coupled to the titling table via the first end of the first support member and the second end of the roller assembly being coupled to the first vertical shuttle such that a combination of the first actuator coupled to the first vertical shuttle and the roller assembly may modify the height of the tilting table as the first vertical shuttle moves.

8. The system for rehabilitation of claim 7, wherein the plurality of roller pairs are made of a plastic and are configured to function as vibration dampeners and motion guides.

9. The system for rehabilitation of claim 6, further comprising
a slit-pinion mechanism including a first end and a second end, the first end of the slit-pinion mechanism being coupled to the tilting table and the second end of the slit-pinion mechanism being coupled to the second vertical shuttle such that a combination of the second actuator coupled to the second vertical shuttle and the slit-pinion mechanism may modify the tilt angle of the tilting table as the second vertical shuttle moves.

10. The system for rehabilitation of claim 9, wherein the slit-pinion performs a rotary tilting movement of the tilting table.

11. The system for rehabilitation of claim 6, further comprising
a vertical linkage system coupling the first actuator coupled to the first vertical shuttle and the second actuator coupled to the second vertical shuttle such that the first actuator may modify the height of the tilting table without modifying the tilt angle of the tilting table.

12. The system for rehabilitation of claim 6, wherein the second actuator has a thirty inch effective stroke span.

13. The system for rehabilitation of claim 12, wherein the system may utilize twenty-four inches of the thirty inch effective stroke span of the second actuator and thereby provide for a +20° to −15° angle adjustment range of tilting table.

14. A method for rehabilitation comprising:
providing a forearm support adapted for receiving a forearm of a user on a tilting table, the tilting table adapted to be moveable in at least one degree of freedom;

displaying an animated or virtual reality sequence on a display coupled to a vertical support and positioned above the tilting table; and tracking movements of the forearm interaction with an exercise simulation, wherein at least one infrared emitter tracks the movements and the at least one infrared emitter is coupled to the vertical support via a support bar such that the at least one infrared emitter tracks the movements of the forearm interaction with the exercise simulation regardless of a tilt angle of the tilting table.

* * * * *